United States Patent
Kirszenberg et al.

(10) Patent No.: US 11,416,963 B2
(45) Date of Patent: Aug. 16, 2022

(54) SYSTEMS AND METHODS TO PROCESS ELECTRONIC IMAGES TO PROVIDE IMPROVED VISUALIZATION AND RENDERING OF HISTOPATHOLOGY SLIDES

(71) Applicant: PAIGE.AI, Inc., New York, NY (US)

(72) Inventors: Alexandre Kirszenberg, New York, NY (US); Razik Yousfi, New York, NY (US); Thomas Fresneau, New York, NY (US); Peter Schueffler, New York, NY (US)

(73) Assignee: PAIGE.AI, INC., New York, NY (US)

( * ) Notice: Subject to any disclaimer, the term of this patent is extended or adjusted under 35 U.S.C. 154(b) by 0 days.

(21) Appl. No.: 17/398,388

(22) Filed: Aug. 10, 2021

(65) Prior Publication Data
US 2022/0051364 A1     Feb. 17, 2022

Related U.S. Application Data

(60) Provisional application No. 63/064,401, filed on Aug. 11, 2020.

(51) Int. Cl.
*G06T 1/60*     (2006.01)
*G06V 20/69*    (2022.01)
(Continued)

(52) U.S. Cl.
CPC .............. *G06T 1/60* (2013.01); *G06T 7/0012* (2013.01); *G06V 20/69* (2022.01); *H04N 5/2259* (2013.01);
(Continued)

(58) Field of Classification Search
CPC ........................................................ G06T 1/60
(Continued)

(56) References Cited

U.S. PATENT DOCUMENTS

| 2008/0291201 | A1* | 11/2008 | Lafon | G06T 15/205 |
| | | | | 345/427 |
| 2019/0156159 | A1* | 5/2019 | Kopparapu | G16H 50/20 |
| 2019/0294628 | A1* | 9/2019 | Smart | G06F 16/5866 |

FOREIGN PATENT DOCUMENTS

| WO | 2005094462 A2 | 10/2005 |
| WO | 2012097438 A2 | 7/2012 |

(Continued)

OTHER PUBLICATIONS

Nokia, "HEIF: Comparison with other formats", current version of webpage: https://nokiatech.github.io/heif/comparison.html; version of webpage as of Aug. 7, 2020: https://web.archive.org/web/20200807033756/https://nokiatech.github.io/heif/comparison.html.
(Continued)

*Primary Examiner* — Amir Shahnami
(74) *Attorney, Agent, or Firm* — Bookoff McAndrews, PLLC

(57) ABSTRACT

A method for processing an electronic image including receiving, by a viewer, the electronic image and a FOV (field of view), wherein the FOV includes at least one coordinate, at least one dimension, and a magnification factor, loading, by the viewer, a plurality of tiles within the FOV, determining, by the viewer, a state of the plurality of tiles in a cache, and in response to determining that the state of the plurality of tiles in the cache is a fully loaded state, rendering, by the viewer, the plurality of tiles to a display.

18 Claims, 14 Drawing Sheets

(51) Int. Cl.
 G06T 7/00 (2017.01)
 H04N 5/225 (2006.01)
 H04N 5/232 (2006.01)
(52) U.S. Cl.
 CPC ..... *H04N 5/23293* (2013.01); *H04N 5/23296* (2013.01)
(58) Field of Classification Search
 USPC ........................................................ 345/534
 See application file for complete search history.

(56) References Cited

FOREIGN PATENT DOCUMENTS

| WO | 2013048640 A1 | 4/2013 |
|---|---|---|
| WO | 2020051113 A1 | 3/2020 |
| WO | 2020243556 A1 | 12/2020 |

OTHER PUBLICATIONS

Wikipedia, "Scrum (software development)", version of webpage as of Jul. 26, 2020: https://en.wikipedia.org/w/index.php?title=Scrum_(software_development)&oldid=969619095.
Wikipedia, "Software development kit", version of webpage as of Jun. 8, 2020: https://en.wikipedia.org/w/index.php?title=Software_development_kit&oldid=961408787.
Wikipedia, "Single instruction, multiple data", version of webpage as of Aug. 9, 2020: https://en.wikipedia.org/w/index.php?title=SIMD&oldid=972038390.
Wikipedia, "Time to first byte", version of webpage as of Feb. 17, 2020: https://en.wikipedia.org/w/index.php?title=Time_to_first_byte&oldid=941283786.
Wikipedia, "Virtual Network Computing", version of webpage as of Mar. 7, 2020: https://en.wikipedia.org/w/index.php?title=Virtual_Network_Computing&oldid=944396374.
Wikipedia, "WebAssembly", version of webpage as of Aug. 8, 2020: https://en.wikipedia.org/w/index.php?title=WebAssembly&oldid=971768638.
510(k) Clearances "Section 510(k) of the Food, Drug and Cosmetic Act requires device manufacturers who must register, to notify FDA of their intent to market a medical device at least 90 days in advance", current version of webpage: https://www.fda.gov/medical-devices/device-approvals-denials-and-clearances/510k-clearances ; version of webpage as of Sep. 4, 2018: https://web.archive.org/web/20200626201146/https://www.fda.gov/medical-devices/device-approvals-denials-and-clearances/510k-clearances.
Jakob Nielson "Website Response Times" NN/g Nielsen Norman Group, Jun. 20, 2010, current version of webpate: https://www.nngroup.com/articles/website-response-times/; version of webpage as of Aug. 9, 2020: https://web.archive.org/web/20200809075624/https://www.nngroup.com/articles/website-response-times/.
Catalln Clmpanu "Microsoft: 70 percent of all security bugs are memory safety issues" percentage of memory safety issues has been hovering at 70 percent for the past 12 years, Feb. 11, 2019. current version of webpage: https://www.zdnet.com/article/microsoft-70-percent-of-all-security-bugs-are-memory-safety-issues/ ; version of webpage as of Jul. 17, 2020: https://web.archive.org/web/20200717140820/https://www.zdnet.com/article/microsoft-70-percent-of-all-security-bugs-are-memory-safety-issues/.
Memory safety "The Chromium Projects" current version of webpage: https://www.chromium.org/Home/chromium-security/memory-safety ; version of webpage as of Jul. 8, 2020: https://web.archive.org/web/20200807183028/https://www.chromium.org/Home/chromium-security/memory-safety.
ACTIX web "A powerful, pragmatic, and extremely fast web framework for Rust" current version of webpage: https://actix.rs/ ; version of webpage as of Jul. 13, 2020: https://web.archive.org/web/20200713161958/https://actix.rs/.

TechEmpower "Web Framework Benchmarks" T-cells that target Lethargic Software Syndrome, current version of webpage: https://www.techempower.com/benchmarks/ ; version of webpage as of Aug. 7, 2020: https://web.archive.org/web/20200807191638/https://www.techempower.com/benchmarks/.
Wikipedia "Tagged Image File Format", version of webpage as of Jul. 26, 2020: https://en.wikipedia.org/w/index.php?title=TIFF&oldid=969688829.
Wikipedia "Lempel-Ziv-Welch", version of webpage as of May 25, 2020: https://en.wikipedia.org/w/index.php?title=Lempel%E2%80%93Ziv%E2%80%93Welch&oldid=958784425.
JPEG "Overview of JPEG 1" current version of webpage: https://jpeg.org/jpeg/ ; version of webpage as of Aug. 9, 2020: https://web.archive.org/web/20200809233804/https://jpeg.org/jpeg/.
JPEG "Overview of JPEG 200", current version of webpage: https://jpeg.org/jpeg2000/index.html; version of webpage as of Aug. 9, 2020: https://web.archive.org/web/20200809232724/https://jpeg.org/jpeg2000/index.html.
Github, Mozilla JPEG Encoder Project "mozilla/mozjpeg: Improved JPEG encoder", current version of webpage: https://github.com/mozilla/mozjpeg ; version of webpage as of Jul. 10, 2020: https://web.archive.org/web/20200710230316/https://github.com/mozilla/mozjpeg.
WebP "An image format for the web", current version of webpage: https://developers.google.com/speed/webp ; version of webpage as of Aug. 10, 2020: https://web.archive.org/web/20200810164758/https://developers.google.com/speed/webp/.
Wikipedia "High Efficiency Image File Format" (HEIF), version of webpage as of Jul. 9, 2020: https://en.wikipedia.org/w/index.php?title=High_Efficiency_Image_File_Format&oldid=966795613.
GitHub, Cyril Concolato et al. "AV1 Image File Format (AFIF)", current version of webpage: https://aomediacodec.github.io/av1-avif/ ; version of webpage as of Aug. 6, 2020: https://web.archive.org/web/20200806170552/https://aomediacodec.github.io/av1-avif/.
FLIF "FLIF—Free Lossless Image Format", current version of webpage: https://flif.info/ ; version of webpage as of Jul. 27, 2020: https://web.archive.org/web/20200727013520/http://flif.info/.
JPEG "Overview of JPEG XL", current version of webpage: https://jpeg.org/jpegxl/ ; version of webpage as of Aug. 6, 2020: https://web.archive.org/web/20200806184032/https://jpeg.org/jpegxl/.
WebP "WebP Compression Study", current version of webpage: https://developers.google.com/speed/webp/docs/webp_study ; version of webpage as of Jun. 25, 2020: https://web.archive.org/web/20200625100545/https://developers.google.com/speed/webp/docs/webp_study.
Daniel Aleksandersen "Comparing AVIF vs WebP file sizes at the same DSSIM", current version of webpage: https://www.ctrl.blog/entry/webp-avif-comparison.html ; version of webpage as of Aug. 10, 2020: https://web.archive.org/web/20200810115203/https://www.ctrl.blog/entry/webp-avif-comparison.html.
FLIF "Lossy FLIF: Advantages of lossy FLIF", current version of webpage: https://flif.info/lossy.html ; version of webpage as of Jul. 5, 2020: https://web.archive.org/web/20200705002145/http://flif.info/lossy.html.
Jon Sneyers "How JPEG XL Compares to Other Image Codecs", current version of webpage: https://cloudinary.com/blog/how_jpeg_xl_compares_to_other_image_codecs ; version of webpage as of Jul. 28, 2020: https://web.archive.org/web/20200728093906/https://cloudinary.com/blog/how_jpeg_xl_compares_to_other_image_codecs.
Jyrki Alakuijala et al. "Benchmarking JPEG XL image compression", current version of webpage: https://www.spiedigitallibrary.org/conference-proceedings-of-spie/11353/113530X/Benchmarking-JPEG-XL-image-compression/10.1117/12.2556264.short?SSO=1 ; version of webpage as of Jun. 13, 2020: https://web.archive.org/web/20200613102034/https://www.spiedigitallibrary.org/conference-proceedings-of-spie/11353/113530X/Benchmarking-JPEG-XL-image-compression/10.1117/12.2556264.short?SSO=1.
Github, Eugene Kliuchnikov et al. "google/brunsli Practical JPEG Repacker", current version of webpage: https://github.com/google/

(56) References Cited

OTHER PUBLICATIONS brunsli ; version of webpage as of Jul. 28, 2020: https://web.archive.org/web/20200728021822/https://github.com/google/brunsli.
Github, Dzmitry Malyshau et al. WebGPU "WebGPU", current version of webpage: https://gpuweb.github.io/gpuweb/ ; version of webpage as of Aug. 8, 2020: https://web.archive.org/web/20200808003414/https://gpuweb.github.io/gpuweb/.
Vulkan Platform Support "Vulkan", current version of webpage: https://www.khronos.org/vulkan/ ; version of webpage as of Aug. 10, 2018: https://web.archive.org/web/20180810065920/https://www.khronos.org/vulkan/.
Steven White et al. "What is Direct3D 12?", current version of webpage: https://docs.microsoft.com/en-us/windows/win32/direct3d12/what-is-directx-12- ; version of webpage as of Oct. 22, 2019: https://web.archive org/web/20191022120451/https://docs.microsoft.com/en-us/windows/win32/direct3d12/what-is-directx-12-.
Apple "Metal: Accelerating graphics and much more", current version of webpage: https://developer.apple.com/metal/ ; version of webpage as of Jul. 14, 2020: https://web.archive.org/web/20200714134955/https://developer.apple.com/metal/.
Gpu "wgpu-rs", current version of webpage: https://wgpu.rs/ ; version of webpage as of Aug. 12, 2020: https://web.archive.org/web/20200812155418/https://wgpu.rs/.
MDN Web Docs "OffscreenCanvas", current version of webpage: https://developer.mozilla.org/en-US/docs/Web/API/OffscreenCanvas ; version of webpage as of Aug. 8, 2020: https://web.archive.org/web/20200808214151/https://developer.mozilla.org/en-US/docs/Web/API/OffscreenCanvas.
MDN Web Docs "SharedArrayBuffer", current version of webpage: https://developer.mozilla.org/en-US/docs/Web/JavaScript/Reference/Global_Objects/SharedArrayBuffer ; version of webpage as of Aug. 8, 2020: https://web.archive.org/web/20200808122842/https://developer.mozilla.org/en-US/docs/Web/JavaScript/Reference/Global_Objects/SharedArrayBuffer.
GitHub "WebAssembly/threads", current version of webpage: https://github.com/WebAssembly/threads ; version of webpage as of Jul. 17, 2020: https://web.archive.org/web/20200717014649/https://github.com/WebAssembly/threads.
MDN Web Docs "Backround Tasks API", current version of webpage: https://developer.mozilla.org/en-US/docs/Web/API/Background_Tasks_API ; version of webpage as of Jul. 13, 2020: https://web.archive.org/web/20200713045949/https://developer.mozilla.org/en-US/docs/Web/API/Background_Tasks_API.
MDN Web Docs "window.requestIdleCallback()", current version of webpage: https://developer.mozilla.org/en-US/docs/Web/API/Window/requestIdleCallback ; version of webpage as of Aug. 4, 2020: https://web.archive.org/web/20200804222903/https://developer.mozilla.org/en-US/docs/Web/API/Window/requestIdleCallback.
Gstreamer "News—GStreamer 1.20.0 new major stable release", current version of webpage: https://gstreamer.freedesktop.org/ ; version of webpage as of Aug. 8, 2020: https://web.archive.org/web/20200808114052/https://gstreamer.freedesktop.org/.
WebRTC "Real-time communication for the web", current version of the webpage: https://webrtc.org/ ; version of the webpage as of Aug. 8, 2020: https://web.archive.org/web/20200808075543/https://webrtc.org/.
The WebM Project "VP9 Video Codec", current version of webpage: https://www.webmproject.org/vp9/ ; version of the webpage as of Aug. 6, 2020: https://web.archive.org/web/20200806232758/https://www.webmproject.org/vp9/.
Wikipedia "An application programming interface (API)", version of webpage as of Aug. 7, 2020: https://en.wikipedia.org/w/index.php?title=API&oldid=971646630.
Wikipedia "Abstract syntax tree", version of webpage as of Aug. 10, 2019: https://en.wikipedia.org/w/index.php?title=Abstract_syntax_tree&oldid=910241958.
Wikipedia "Amazon Web Services", version of webpage as of Aug. 7, 2020: https://en.wikipedia.org/w/index.php?title=Amazon_Web_Services&oldid=971621711.
Wikipedia "Content delivery network", version of webpage as of Aug. 10, 2020: https://en.wikipedia.org/w/index.php?title=Content_delivery_network&oldid=972145057.
Wikipedia "Continuous integration", version of webpage as of Jul. 28, 2020: https://en.wikipedia.org/w/index.php?title=Continuous_integration&oldid=969916004.
Wikipedia "Discrete cosine transform", version of webpage as of Aug. 10, 2020: https://en.wikipedia.org/w/index.php?title=Discrete_cosine_transform&oldid=972220052.
Wikipedia "Deep Zoom", version of webpage as of Feb. 16, 2020: https://en.wikipedia.org/w/index.php?title=Deep_Zoom&oldid=941128067.
Wikipedia "Discrete wavelet transform", version of webpage as of Jul. 9, 2020: https://en.wikipedia.org/w/index.php?title=Discrete_wavelet_transform&oldid=966828588.
Wikipedia "Food and Drug Administration", version of webpage as of Jun. 7, 2020: https://en.wikipedia.org/w/index.php?title=Food_and_Drug_Administration&oldid=961216493.
Wikipedia "File System", version of webpage as of Aug. 2, 2019: https://en.wikipedia.org/w/index.php?title=File_system&oldid=909082892.
Wikipedia "OpenGL Shading Language", version of webpage as of Jul. 20, 2020: https://en.wikipedia.org/w/index.php?title=OpenGL_Shading_Language&oldid=968635606.
Wikipedia "H&E stain", version of webpage as of Jun. 15, 2020: https://en.wikipedia.org/w/index.php?title=H%26E_stain&oldid=962752471.
Wikipedia "Just-in-time compilation", version of webpage as of Aug. 9, 2020: https://en.wikipedia.org/w/index.php?title=Just-in-time_compilation&oldid=971974067.
Wikipedia "LLVM", version of webpage as of Aug. 4, 2020: https://en.wikipedia.org/w/index.php?title=LLVM&oldid=971184873.
cppreference.com "C++ reference", current version and version of webpage as of Jan. 27, 2020: https://en.cppreference.com/mwiki/index.php?title=Main_Page&oldid=115512.

* cited by examiner

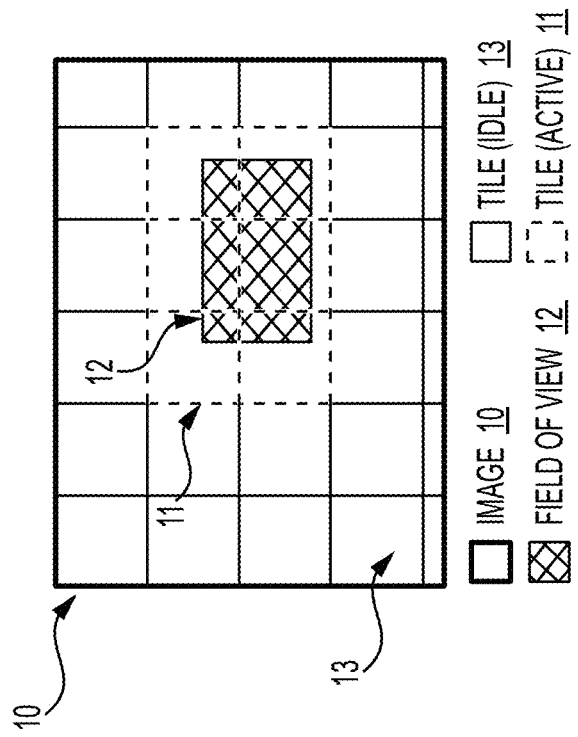
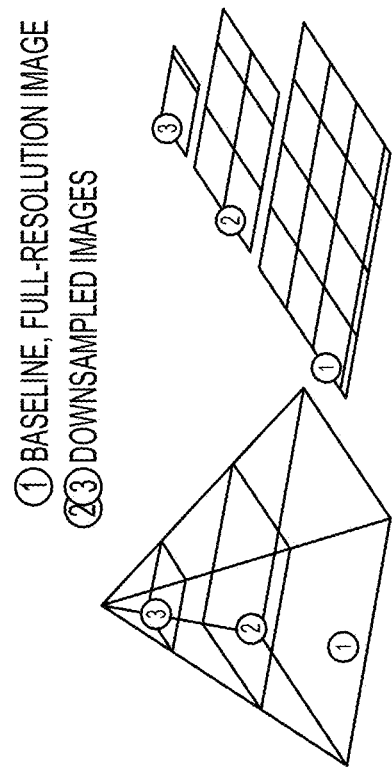
FIG. 2
FIG. 1

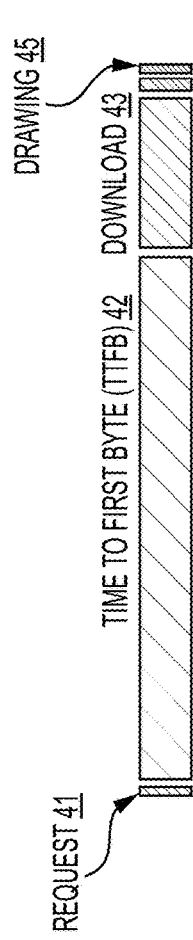
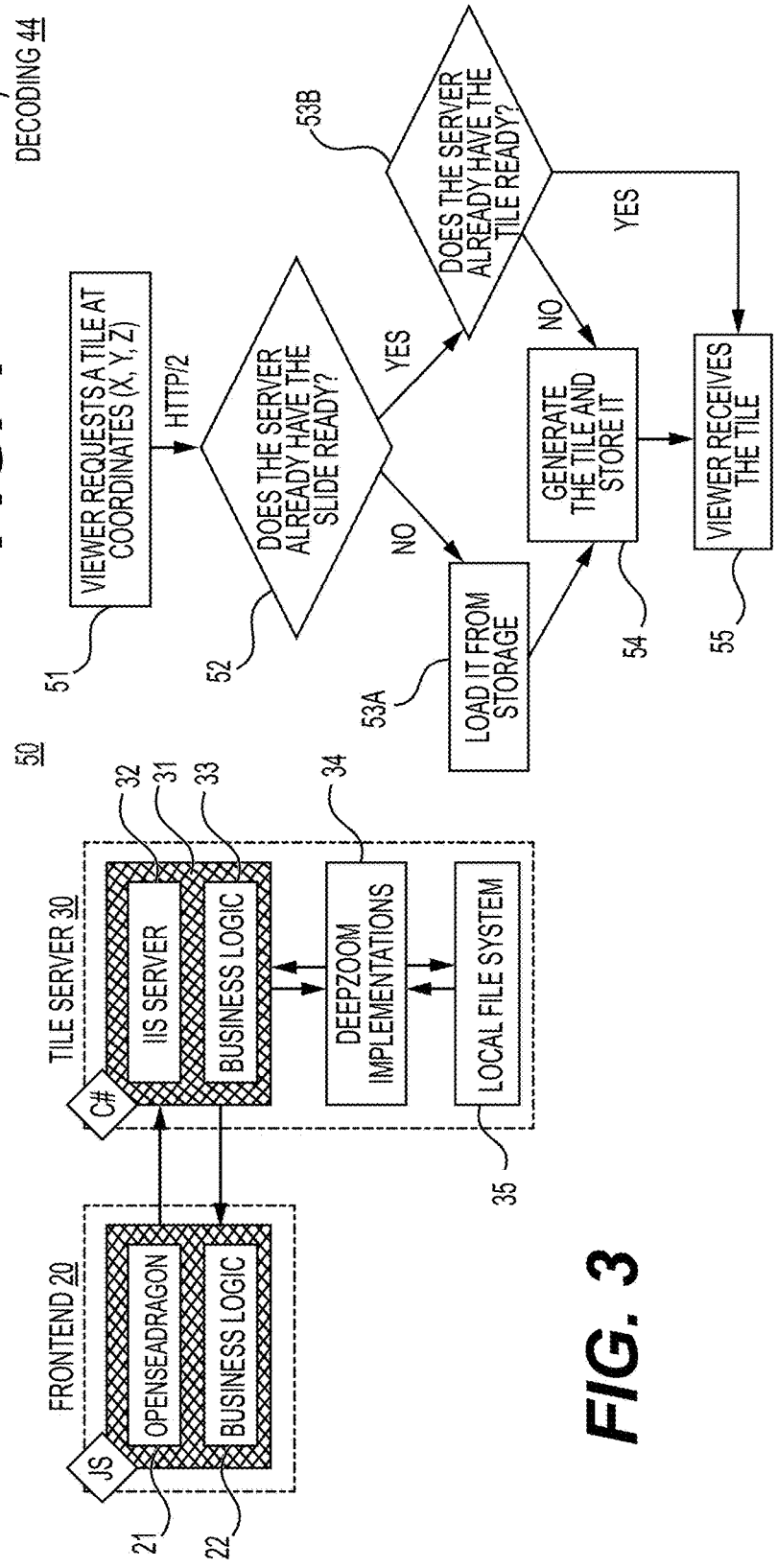

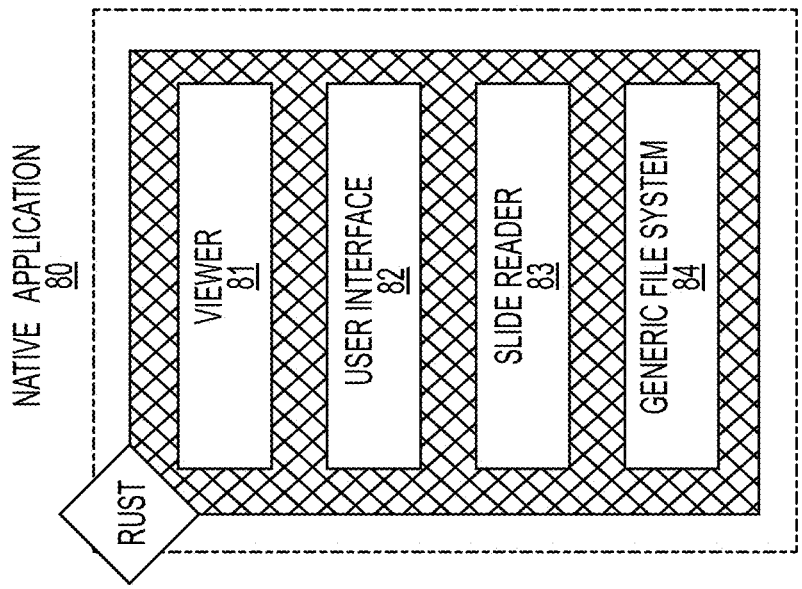
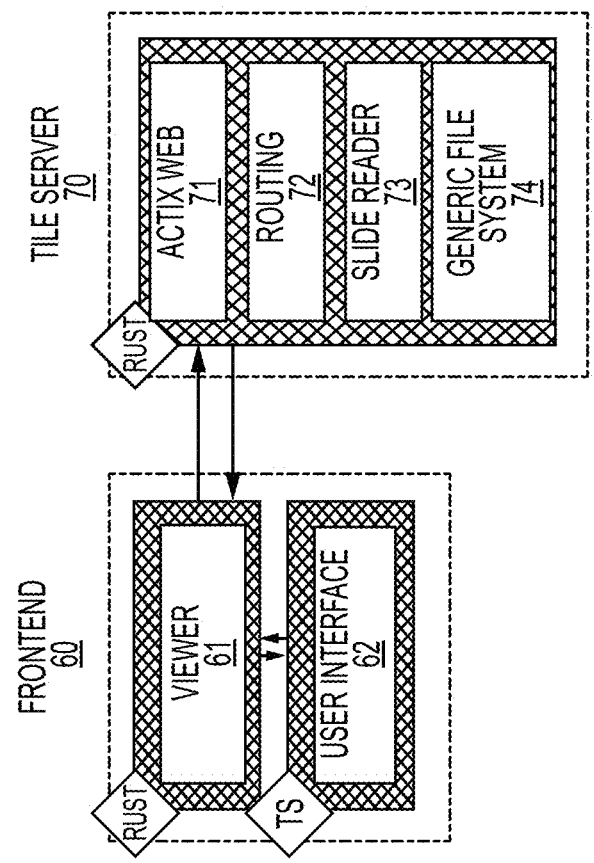
FIG. 6B
FIG. 6A

SYSTEMS AND METHODS TO PROCESS ELECTRONIC IMAGES TO PROVIDE IMPROVED VISUALIZATION AND RENDERING OF HISTOPATHOLOGY SLIDES

RELATED APPLICATION(S)

This application claims priority to U.S. Provisional Application No. 63/064,401 filed Aug. 11, 2020 the entire disclosure of which is hereby incorporated herein by reference in its entirety.

FIELD OF THE DISCLOSURE

Various embodiments of the present disclosure pertain generally to improving the visualization and rendering of histopathology slides. More specifically, particular embodiments of the present disclosure relate to systems and methods for processing electronic images to provide improved visualization and rendering of histopathology slides. The present disclosure further provides systems and methods for using machine learning, artificial intelligence, and computer vision to process electronic images to provide improved visualization and rendering of histopathology slides.

BACKGROUND

Histopathology slides are tissue sections extracted from a biopsy and placed on a glass slide for microscope inspection. In order for the tissue to be visible under a microscope, these sections are stained with one or more pigments, the most common of which is Hematoxylin and Eosin (H&E) which give slides their remarkable pink hue. While these slides may be historically examined under a microscope, recent years have seen a push for digital pathology. In digital pathology, slides may be scanned at very high resolutions to be later viewed on a monitor. While digital pathology provides certain advantages, it can be challenging to scan and visualize slides with sufficient resolution to provide for desired images and fields of view.

The foregoing general description and the following detailed description are exemplary and explanatory only and are not restrictive of the disclosure. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for processing electronic images to provide improved visualization and rendering of histopathology slides.

A computer-implemented method for processing an electronic image, the method comprising: receiving, by a viewer, the electronic image and a FOV (field of view), wherein the FOV includes at least one coordinate, at least one dimension, and a magnification factor, loading, by the viewer, a plurality of tiles within the FOV, determining, by the viewer, a state of the plurality of tiles in a cache; and in response to determining that the state of the plurality of tiles in the cache is a fully loaded state, rendering, by the viewer, the plurality of tiles to a display.

A computer system for processing an electronic image, the computer system comprising at least one memory storing instructions, and at least one processor configured to execute the instructions to perform operations comprising: receiving, by a viewer, the electronic image and a FOV (field of view), wherein the FOV includes at least one coordinate, at least one dimension, and a magnification factor, loading, by the viewer, a plurality of tiles within the FOV, determining, by the viewer, a state of the plurality of tiles in a cache; and in response to determining that the state of the plurality of tiles in the cache is a fully loaded state, rendering, by the viewer, the plurality of tiles to a display.

A non-transitory computer-readable medium storing instructions that, when executed by a processor, cause the processor to perform operations for processing an electronic image, the operations comprising: receiving, by a viewer, the electronic image and a FOV (field of view), wherein the FOV includes at least one coordinate, at least one dimension, and a magnification factor, loading, by the viewer, a plurality of tiles within the FOV, determining, by the viewer, a state of the plurality of tiles in a cache; and in response to determining that the state of the plurality of tiles in the cache is a fully loaded state, rendering, by the viewer, the plurality of tiles to a display.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 1 depicts a pyramidal structure of a whole slide image, according to an exemplary embodiment of the present disclosure.

FIG. 2 depicts a Field of View (FOV) of an exemplary viewer, according to an embodiment of the present disclosure.

FIG. 3 depicts an architecture of an exemplary viewer, according to an embodiment of the present disclosure.

FIG. 4 illustrates a timing breakdown of an exemplary tile request from a viewer, according to an embodiment of the present disclosure.

FIG. 5 is a flowchart illustrating a control flow of an exemplary tile request, according to an embodiment of the present disclosure.

FIG. 6A is an architecture of a viewer, according to an embodiment of the present disclosure.

FIG. 6B is an architecture of a native application of a viewer, according to an embodiment of the present disclosure.

DESCRIPTION OF THE EMBODIMENTS

Figure 7A:
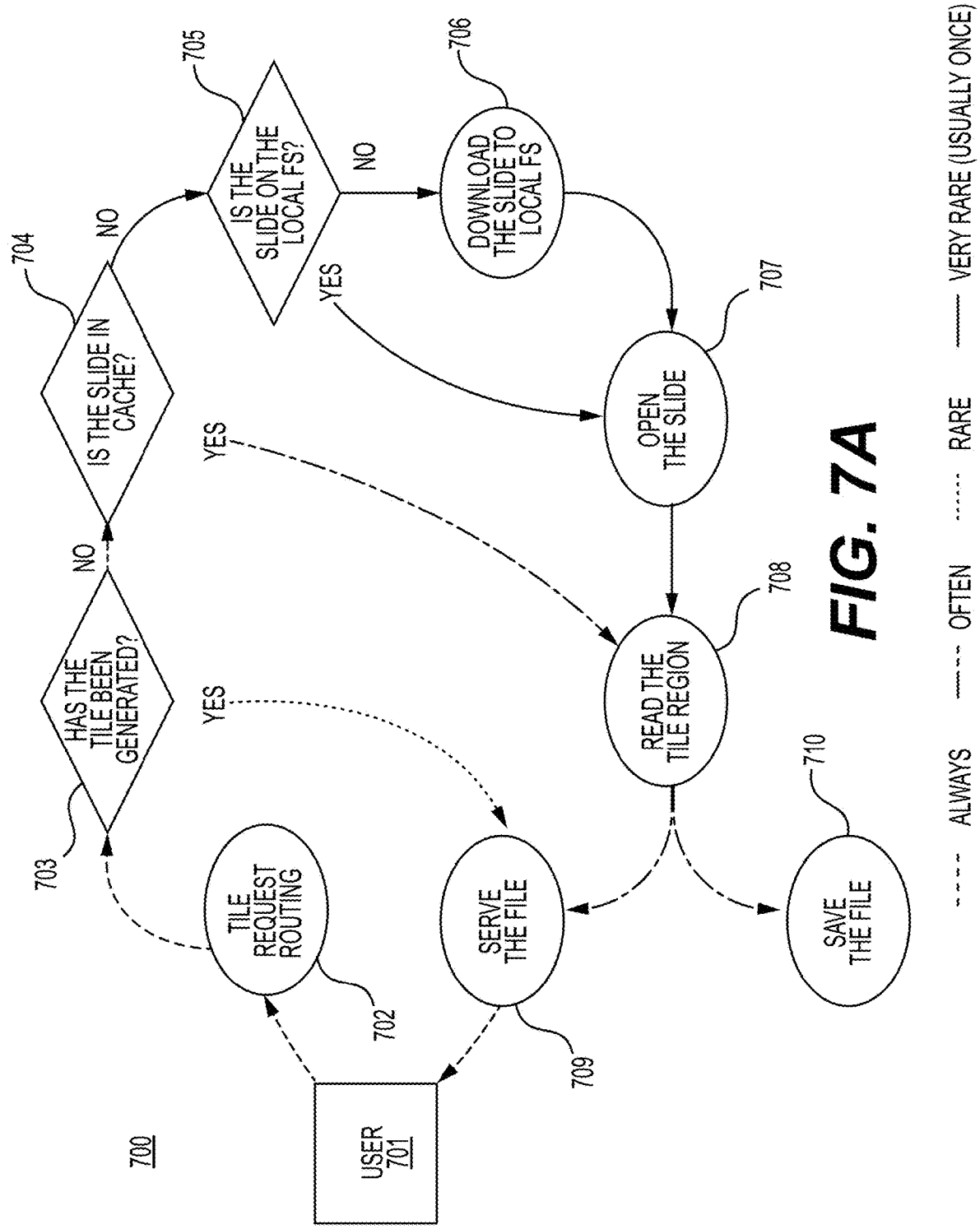
FIG. 7A is a flowchart illustrating a control flow of a tile request, according to an embodiment of the present disclosure.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Scanner manufacturers often maintain their own software to visualize slides alongside their scanner. They may also enable third-party software to open and read these slides in much the same fashion. These software packages or modules are commonly called slide viewers. The present disclosure includes, among other things, an exemplary embodiment of a novel slide viewer that can open slides acquired from a variety of scanners. This viewer may run on all modern internet browsers (i.e. Google Chrome, Mozilla Firefox, Microsoft Edge, Apple Safari, etc.). On top of its slide viewing capabilities, the slide viewer may also tie in to other products by featuring advanced medical-grade artificial intelligence inference for cancer detection.

Slide scans are images with resolutions ranging from 20,000×20,000 to over 120,000×120,000 pixels. These images are descriptively called Whole Slide Images (WSIs) and can weigh multiple gigabytes on disk, even after lossy compression, and cannot be efficiently transferred to a client to be viewed in a timely manner. Certain technological obstacles exist with handling large digital images. First, bandwidth is a limiting factor to how much data can be transferred in a specific amount of time. Since the viewer is accessed via the Internet, this bandwidth usually has an upper limit of a few megabytes per second. This means that transferring a gigabyte image would take multiple seconds or even minutes. In addition, substantial processing power may be required in order to decode these images. While a small 256×256 image can be decoded in the order of a millisecond, decoding a gigapixel image will take seconds, if not minutes. Finally, in terms of memory, while the compressed image might weigh in the order of a gigabyte, the uncompressed data is an order of magnitude larger. Such an amount of data will not fit at once in a computer's memory.

One goal is to find ways to improve a current technology stack when it comes to WSIs. A few areas of interest addressed by this disclosure include new ways of streaming histopathology slide data. Current slide viewers may use open source libraries and vendor Software Development Kits (SDKs) to open and read slides. These options are not the most efficient, and better techniques could significantly speed up streaming.

For instance, this could involve changing the data representation format of slides as they are stored on disk to enable new optimizations or to leverage existing optimizations to their fullest. Historically, slides have been stored in their original format, which is fully dependent on the scanner vendor. Different vendors may have different constraints and this means that having no unified format may make it harder to optimize all possible pathways.

New compression techniques may also improve current technology in slide viewing. This axis of research focuses on new compression techniques that can more efficiently store slide image data. For instance, tissue detection algorithms can avoid having to store large parts of the image where no tissues have been detected. Newer image formats might also yield better compression ratios by leveraging more advanced techniques or more computing power during encoding.

Further, server-side rendering may improve current slide viewing technology. Virtual Network Computing (VNC) technologies have proven that it is possible to build real-time interactive experiences by streaming a visual feed to a client, which in turns sends user input to the server. Such an approach may be able to minimize data transfers thanks to performant video codecs while enabling exceptional user experience.

In addition, slide-viewing technology improvements may include frontend rendering techniques. Web browsers have now been able to leverage Graphics Processing Unit (GPU) rendering. The WebGL Application Programming Interface (API) allows a JavaScript application to execute rendering instructions in an idiom inspired by OpenGL, which is the industry standard for 3D rendering. More recently, new APIs such as WebGL 2.0 and WebGPU have gone even further by allowing lower-level access to GPU primitives. These technologies could be applied to the slide viewer in order to speed up the slide viewer and decrease its memory consumption.

In the following sections, specific vocabulary will be used to describe concepts related to an exemplary WSI viewer.

As described above, WSIs are high-resolution image scans of histopathology slides. The resolutions of these images range in the gigapixels. This property makes it impractical to store and display these images in a conventional manner. Indeed, it is very difficult to decode a whole image in memory as it would come to occupy tens of gigabytes, which is more than the memory endowment of many personal computers available today. Furthermore, it would be also be difficult to display the whole image, since monitor resolutions are closer to the megapixels.

Therefore, WSIs are encoded in such a way that they allow for region decoding. Each region of the image may be displayed without having to read or decode the whole image with it. As mentioned before, the monitor that a pathologist uses to view a slide typically cannot display the full resolution image. As a result, typically only the region that is currently presented on screen may be decoded and sent to the client. This optimization makes it possible to index and read into WSIs in real-time.

However, this approach falls short if the pathologist decides to zoom out and display the whole slide on screen. In order to show even a downsampled version of the full image, it may still be necessary to read it entirely. To remedy this, on top of the full resolution baseline image, WSIs also include intermediate magnification levels with smaller resolutions, all the way down to a thumbnail image that can fit on the screen. Such an organization is often referred to as a pyramidal structure, where the base of the pyramid is the baseline image, and each level above may be an intermediate magnification level.

In order to allow for region decoding, each level may be cut into tiles in a regular grid. These tiles may be randomly accessed. In order to decode a region of the image, only the tiles that overlap it may need to be read and decoded. FIG. 1 is a schema of this pyramidal structure.

As shown in FIG. 1, the pyramidal structure has a baseline image 1 comprising a full resolution image. At least one downsampled image, i.e., downsampled images 2 and 3 in FIG. 1, may be placed on top of the baseline image 1. The baseline image 1, as well as downsampled images 2 and 3 may be cut into the regular grid as described above.

The Field Of View (FOV) of the viewer is the area of the image that is currently on display. It can be thought of as the grouping of coordinates (x, y), dimensions (w, h), and magnification factor z. The magnification factor may determine which level of the WSI is best suited for display, while the coordinates and dimensions may determine which region of the level image should be decoded.

FIG. 2 shows how only a few active tiles 11 of the level image 10 may need to be decoded in order to display the requested FOV 12. The idle tiles 13 may not be included in the FOV 12.

When the FOV 12 moves, the active tiles 11 will change. Only the tiles that are currently needed for display might need to be kept in memory. As such, the graphics memory needed may be a function of the resolution of the display, and not a function of the size of the image.

In order to better identify the different areas to improve, one possible approach was to take a closer look at the architecture of exemplary slide viewers. The architecture of an exemplary slide viewer is illustrated in FIG. 3. The exemplary slide viewer may be composed of a frontend 20 and a backend ("tile server") 30. The frontend 20 may be responsible for displaying the WSIs to the user, while the backend 30 may be responsible for communicating the potentially necessary data to the frontend. More detail about exemplary components are disclosed in the following sections.

Since the user may access an exemplary slide viewer through a web browser, the frontend 20 (as illustrated in FIG. 3) may be a web application written in JavaScript. The exemplary slide viewer may make extensive use of a viewer 21, such as the OpenSeadragon open-source library, which is a web-based viewer for high-resolution images.

The viewer 21, for example OpenSeadragon, may handle some or all the rendering of WSIs, as well as user interactions such as panning, zooming, and jumping around using the "Slide Navigation" panel. The user may drag the screen with the mouse to pan the display, while scrolling zooms in and out. There may be additional features such as rotating the display, measuring physical distances, drawing annotations on the canvas, and others.

As disclosed above, WSIs are divided into multiple magnification levels and cut into tiles (see pyramid of FIG. 1). In order to display a given FOV, the viewer 21 (such as OpenSeadragon) loads all the tiles that cover the FOV from a backend 30, which may also be called a tile server.

OpenSeadragon is a robust solution for viewing high resolution images. However, compared to some other high-resolution image viewer solutions targeting the web platform, OpenSeadragon is not always able to maintain a constant 60 Frames Per Second (FPS) during user interaction. This may make for a sub-optimal user experience. Seadragon also may only support rendering using only the 2D browser canvas Application Programming Interface (API). As a result, WebGL may be used as a more performant API that can take better advantage of the graphical capabilities of the client.

OpenSeadragon is not be the only possible solution available for viewing large images in a browser. Other suitable viewer solutions include OpenLayers, Leaflet, MapBox, and DeckGL. All of these solutions are tailored for geographic data, but may be adapted to support 2D pixel data. Some of these solutions support WebGL and have good performance. However, they may include features that are not needed. As a result, the surface areas of the possible solutions may be quite large, which makes modification harder.

The frontend 20 may also include a business logic algorithm 22.

The backend 30 of the exemplary slide viewer may comprise a web server 31 written in C#. The web server 31 may leverage software on an IIS web server 32 to efficiently serve HTTP requests.

The backend 30 is one component of interest in the exemplary viewer: given a request for a tile of dimensions (w, h) at coordinates (x, y) and magnification level z, the backend 30 returns the corresponding image. Since an exemplary slide viewer may support a number of WSI formats, the backend 30 may call into different implementations 34, such as Deep Zoom implementations 34, as illustrated in FIG. 3. These implementations 34 own the logic that decodes the requested image regions from the original WSI files. Generally, WSI files may be stored on the file system 35 associated with the backend 30.

Deep Zoom is a technology for streaming and visualizing very large images. A Deep Zoom Image (DZI) is composed of two parts: a DZI file and a directory. A DZI file (.dzi) describes the format of the image for the purpose of visualization. Two important properties may be the tile size and baseline resolution, from which it is possible to infer some or all intermediate magnification levels by multiplying the baseline resolution with negative powers of two. For instance, with a baseline resolution of 1024×1024, the first intermediate level will have a resolution of 512×512, the second of 256×256, etc. Aside from the DZI file, the directory may contain some or all tile images, themselves arranged in folders corresponding to the different magnification levels. For instance, the file stored under the path tiles/3/1_2.jpg corresponds to the tile at magnification level z=3, and at coordinates (x, y)=(1, 2). At z=3, the level resolution is an eighth of the baseline images.

In terms of the performance of a web server, tile requests should be near-instantaneous. In order for the viewer to feel responsive, tile requests may need to have low-latency and high-throughput. As such, the pipeline for retrieving and serving tiles may need to be kept as short as possible, using the fastest technology available. In this case, using a full-blown web server such as IIS may be overkill.

It may be possible to build low-latency systems in C#, but the language may make it difficult. C# is a difficult collected language: memory allocations are automatic, and the process may occasionally traverse a graph of allocated objects to determine which can be deallocated and memory freed. This means that C# is completely memory-safe, and the programmer seldom needs to worry about memory management. However, this procedure is not without a cost, and can cause latency spikes when it runs at the same time as a request is pending. Furthermore, garbage collected languages may use more memory on average in order to keep track of object liveness. Finally, compiled C# code runs on a virtual machine, which takes its own performance and memory usage toll. On a personal machine, the development version of the server may take a full minute and allocate up to 700 MB of memory before it can start answering HTTP requests. Both of these numbers may be significantly reduced with a different implementation and backing technology.

FIGS. 4 and 5 provide a quick overview of the timing and control flow of a tile request from a user's perspective. The control flow of the tile request is a simplified version of the underlying algorithms As shown in FIG. 4, a timeline metric may comprise the relative times that may be taken for a request 41, a Time To First Byte (TTFB) 42, a download 43, a decoding 44, and a drawing 45. Slow paths, such as a download 43 are represented in a striped pattern, and slow operations, such as TTFB, are represented in another pattern with thicker stripes. The request 41 may comprise a relatively short time within the control flow of a tile request, whereas the TTFB may take a comparatively much longer time. The Time To First Byte (TTFB) 42 metric represents the latency of the server, and is a metric that may be focused on the most in regards to the rest of the present disclosure. The download 43 may also take a comparatively long time within the control flow, while the decoding 44 and the drawing 45 steps may be completed relatively quickly.

FIG. 5 is a flowchart illustrating an overview method 50 of the timing and control flow of a tile request from a user's perspective.

In step 51, the method may include a viewer requesting a tile at coordinates (x, y, z). This request may be sent via HTTP protocol.

In step 52, a server, such as tile server or backend 30 as shown in FIG. 3, may receive the request and may determine whether the server already has a requested tile ready.

In step 53*a*, if the server has determined that the slide is not ready, the server may load the slide from a storage device.

In step 53*b*, if the server instead determines that the slide is already ready, the method may include the server may then determining whether the server already has a tile at the requested coordinates ready.

In step 54, if the slide has been loaded from storage or if the server does not already have the tile ready, the method may include the server generating the requested tile and storing it.

In step 55, the method may include the viewer receiving the tile from the server, either as generated in step 54 or as already processed by the server in step 53*b*.

An exemplary embodiment of the slide viewer has two goals. First, the slide viewer should be fast. Users may not have to wait long before FOVs load in, and the viewer should maintain a constant 60 FPS when panning and zooming. Pathologists are used to the microscope, where latency is bounded only by the speed of light. With an exemplary viewer, it may be preferable to strive to replicate this experience as close as possible. The end goal is to have no perceivable latency. For reference, a response time of 100 ms is considered as the upper limit for giving users a feeling of instantaneous feedback.

Secondly, the slide viewer has a need to be measurable. It may be important to be able to provide precise metrics as to how the exemplary viewer performs under use. For comparison to existing slide viewers, a benchmark suite representative of a realistic load is needed.

Generally, there is one constant to a web application such as a slide viewer. JavaScript has predominately been the language of the web, and was previously the only language browsers will natively run.

Recently, browsers have started to implement a virtual machine to run WebAssembly (Wasm), which is a type of assembly code targeting the web platform. As security is of paramount importance in a browser, it is designed to be fully sandboxed. It is undesirable to visit a website only for it to have complete access over the machine. Aside from that advantage of Wasm: it is also much faster to execute than JavaScript. In order for a browser to execute JavaScript, the following steps may be executed:

a. Downloading the original JavaScript source.
    b. Parsing the JavaScript into an Abstract Syntax Tree (AST).
    c. Compiling the JavaScript into machine code, which may vary between implementations. Historically, JavaScript was an entirely interpreted language. With the advent of Just In Time (JIT) compilation, it is now common to refer to it as a compiled language.
    d. Executing the JavaScript.

The above steps illustrate an overview of the process. In practice, some of the steps may be partially skipped. For example, the browser's JavaScript engine does not need to parse the entire JavaScript source in order to start executing it. In fact, it can use its lexer to quickly jump over whole sections of code that might not be necessary for first execution. This may be referred to as lazy compilation.

However, some steps cannot be completely optimized away. Even though modern JavaScript code is minified and compressed before being sent to the client, it weighs more than raw bytecode would. Similarly, while parsing can be skipped in some cases, it will need to happen at some point. JIT compilation may have impressive performance, but it involves an additional step at runtime.

As a byte code, Wasm provides an elegant solution to most of these issues. But more importantly, Wasm is a compilation target. This means that any language that implements a Wasm backend may be able to run in a browser2, which is an extremely exciting development in the history of the web.

Rust is a new, modern language that has a lot of interesting properties: like C and C++, the language features manual memory management, which allows for precise control over the patterns of memory consumption of a pro-gram.

However, unlike both C and C++, Rust is memory-safe. Thanks to the inclusion of a new concept called lifetimes and built-in Resource Acquisition Is Initialization (RAII), much of the complexity and volatility of manual memory management is taken care of by the compiler itself. This is considered the defining feature of Rust: it eliminates a whole class of programmer errors by forbidding provably unsafe operations by default.

Rust defers to the LLVM (low level virtual machine) backend for compilation. Thus, Rust may take advantage of the many optimizations provided by the LLVM compiler, which may result in code that is as fast, and sometimes faster, than its C/C++ counterpart. Further, all LLVM targets may be natively supported, including Linux, Windows, macOS, etc. This list may also include Wasm.

Rust also includes a slew of others features to be expected in a modern programming language, such as but not limited to: an advanced type system; zero-cost abstractions; pattern matching; functional primitives; asynchronous programming; built-in package manager and compilation toolchain; built-in automatic code formatting and linting; and automatic C and C++ bindings generation. Rust is still evolving rapidly and may offer even more improvements, while maintaining a strict backwards-compatibility policy. Rust has risen in popularity due to its raw performance and iteration speed. The combination of manual memory management and native targets means that there may not be any artificial boundary to how fast Rust can run. Furthermore, since Rust is not garbage collected, performance is predictable: there is no "lag spike" effect. Importantly, Rust is safe—it has been shown that 70% of all serious security bugs were caused by memory safety issues. Rust may also be run in the browser, meaning that a user may leverage all of the advantages of a Rust codebase and Wasm performance with none of the historical drawbacks associated with web applications. This also makes it possible to share code between browser and native targets. Notwithstanding the foregoing, it is contemplated that any desired language or code base, currently existing or future developed, may be used to run the web server and/or slide viewer consistent with the embodiments of this disclosure.

FIG. 6A is an exemplary schema of an exemplary embodiment of a slide viewer 100. On the frontend 60, the core viewer 61 and rendering logic may be written in Rust, while the higher-level user interface logic 62 may be written in TypeScript6 with React7. For the tile server or backend 70, a web server 71, such as an Actix Web web server, currently considered one of the most performant web servers, may be used. A routing logic 72, an image decoding or slide reader logic 73, and a file system logic 74, may all be written in Rust. However, within the scope of this exemplary embodiment, support may also be implemented for Aperio SVS slides. Implementing support for other slide formats may require writing bindings to C++ libraries (e.g. for Philips iSyntax) or re-implementing the decoding logic manually. The viewer core logic may be written in Rust, unlocking new possibilities such as native rendering. By mixing the frontend and tile server codebases, a native version of the viewer may run in a window on Linux, Windows and macOS.

FIG. 6B illustrates an example architecture of such a program. In FIG. 6B, the native application 400 is written in Rust, and comprises a viewer 401, a user interface 402, a slide reader 403, and a generic file system 404.

Anatomy of a Tile Request

Figure 7B:
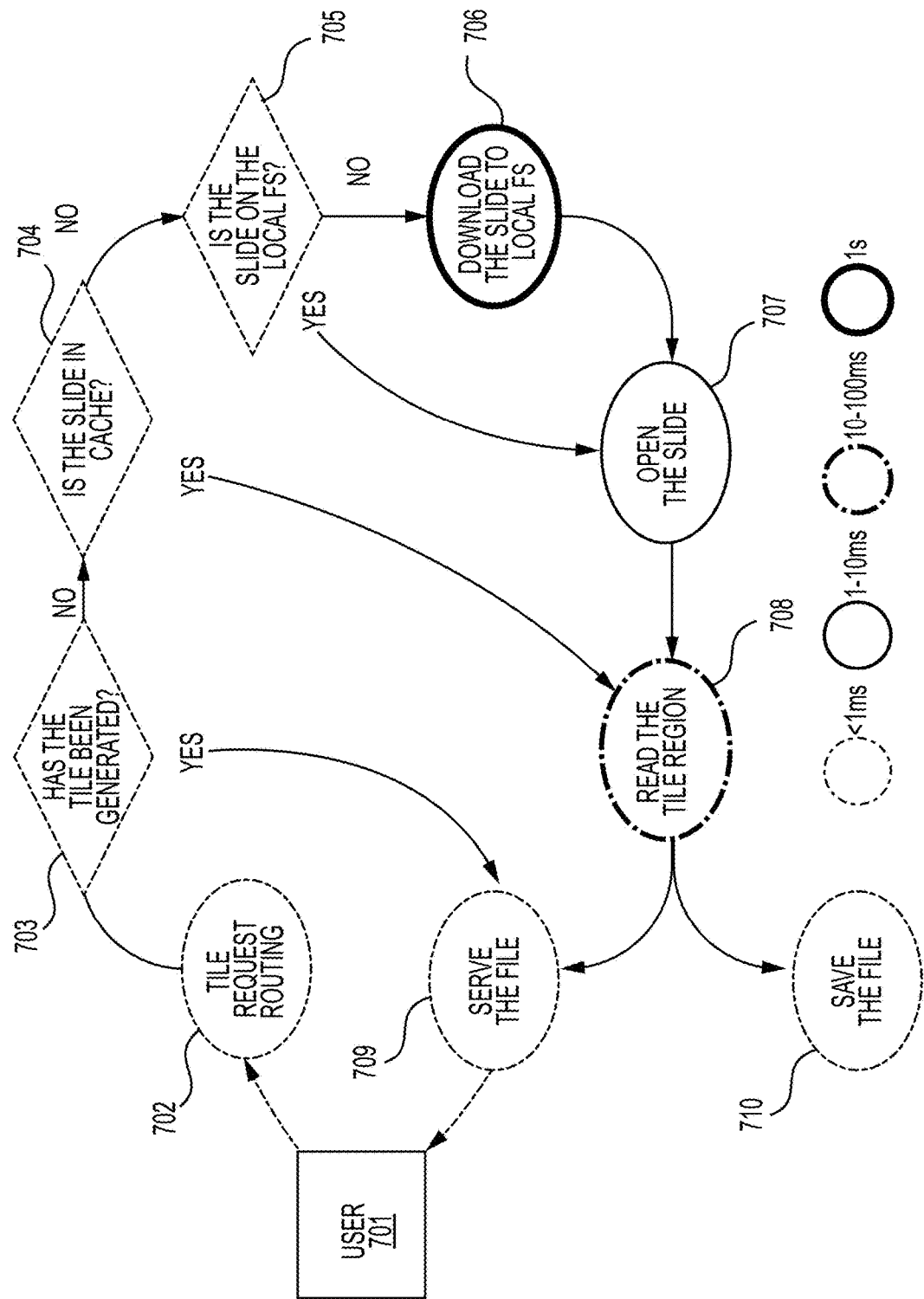
FIG. 7B is a flowchart illustrating a control flow of a tile request with latency indications, according to an embodiment of the present disclosure.

When a user makes a request for a tile at coordinates (x, y) and magnification level z—referred to as coordinates (z, x, y)—the tile server starts the procedure illustrated by FIGS. 7A and 7B. The procedure goes through multiple steps and branches and ends with the user being served an image corresponding to the requested tile.

FIG. 7A is a flow diagram illustrating an exemplary tile request procedure 700 from a user (e.g., steps 702-710), as described above. All steps of the exemplary tile request procedure 700 may be optional and may be completed in any order. The occurrence of each step may also vary, as indicated by the difference in a line pattern between steps. One pattern of dashes in a line may represent that the step always, often or rarely occurs, while a continuous, unbroken line may represent that the step very rarely occurs (i.e., usually only occurs once, such as the occurrence of steps 705, 706, and 707).

In exemplary tile request procedure 700, a user 701 may request a tile from a server. The specific tile request may include more than one tile of a digital image associated with a pathology specimen image, or may be a singular tile of the digital image.

In step 702, the procedure may include routing the tile request to a server.

In step 703, the server may determine whether the tile has been generated by the server. If the tile has been generated by the server, the procedure may advance to step 709, as described below.

If the tile has not been generated by the server yet, the server may then determine, in step 704, whether a slide associated with the requested tile is in a cache. In one case, where the tile requested has not been generated but the WSI is in cache, the server may read the region corresponding to the tile and serves the resulting image file to the user as described in step 708. This file is saved in case the client requests the same tile again, as described in step 710, in which case the procedure may be able to bypass the region decoding step entirely.

If the slide associated with the requested tile is not in cache, then the server may then determine, in step 705, whether the slide is on the local File System (FS). If the slide is on the local file system, then the procedure may advance to step 707, as described below.

If the slide is not on the local file system, then the server may then download the slide to the local file system in step 706. Once the slide is downloaded into the local file system, the server may open the slide in step 707.

In step 708, the server may read the tile region, and may either proceed to save the tile file in a step 710, or may serve the file back to the user 701 in step 709.

When the user requests a slide for the first time, or long enough a time has elapsed since their last request that the slide has left the cache and been cleared from the local FS, the server may need to retrieve the slide from the remote FS (e.g. such as an Amazon Web Services (AWS) S3 bucket) to the local FS and open it. This operation may only happen once, when the client first retrieves the metadata related to a WSI.

The steps described in FIG. 7B, which illustrate the same exemplary tile request procedure 700, may further illustrate a time cost associated to each step, which is referred to as latency incurred. This latency adds up to form the overall latency of the whole request, which the user will experience as the TTFB metric.

The latency incurred by each step may be illustrated by the patterned line around each step. For example, a line with a dotted pattern may indicate that the step has a latency incurred of less than one millisecond, whereas a thinner line may indicate a latency incurred of between one and ten milliseconds, etc.

Figure 8:
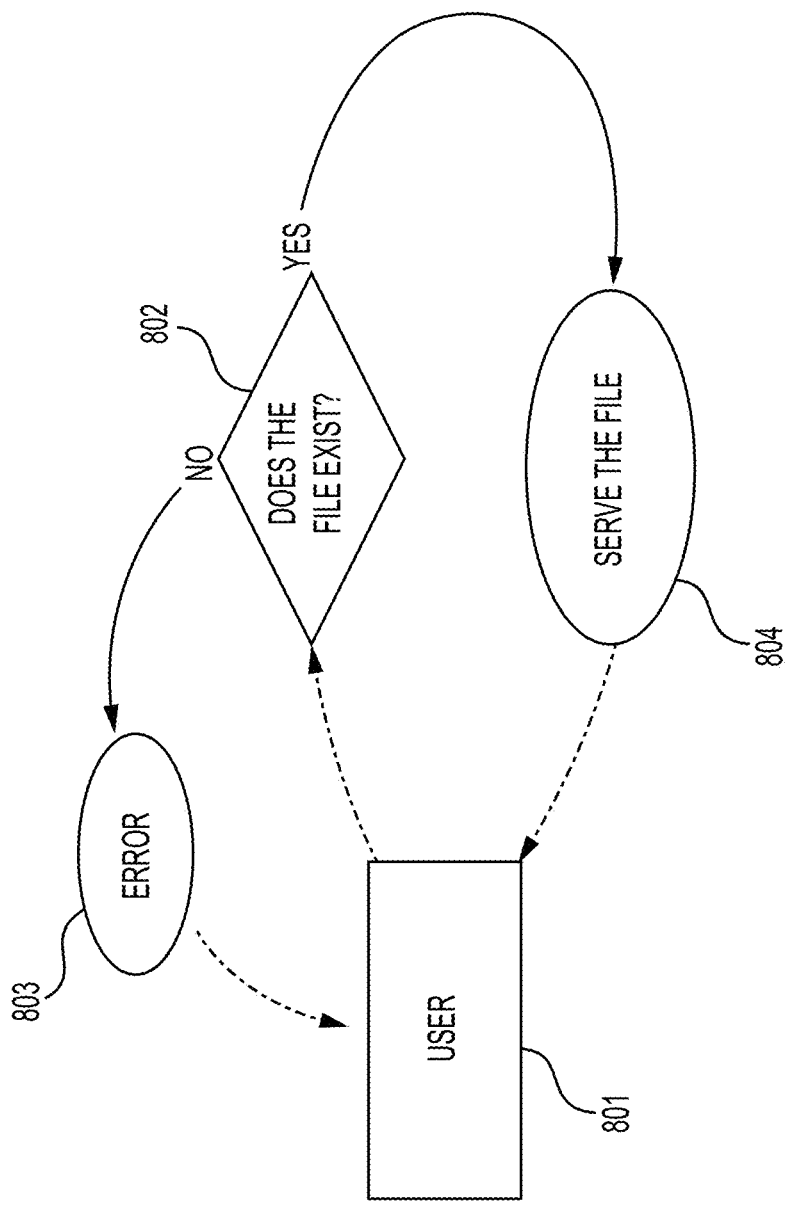
FIG. 8 is a flowchart illustrating a static control flow of a tile request, according to an embodiment of the present disclosure.

FIG. 8 complements FIG. 7 by illustrating the incurred latency at every step. The fastest path may be when the tile has already been generated (determined by the server in step 703) by the server and need only be served. In this case, the tile is present on the FS, and can be streamed directly to the user.

However, the most frequent case is when the tile is not present on the FS and must be generated from the WSI, but the slide is available in cache. Compared to the fastest path, this case entails two additional steps:
 a. Decoding the tile region from the WSI, which is blocking.
 b. Saving the file to the FS, which is non-blocking: the operation happens in parallel to serving the file.

Finally, in the rare case when the slide is not present in cache (as determined by the server in step 704) and possibly not present on the local FS, the server may need to retrieve the WSI file from the FS (as in step 706). As the files are very large, this can take up to a few seconds. Beneficially, this case is usually only hit once when the slide is first requested by the user, which may make its high latency acceptable.

This algorithm may be similar to the one illustrated in FIG. 5. Thanks to the lower overhead of one exemplary embodiment implementation, its average latency may be lower, as demonstrated below.

Region Decoding

The procedure of decoding a region of a WSI may depend entirely on the format of the image.

One such format of the WSI may be in the form of a ScanScope Virtual Slide (SVS) images, which use the TIFF image container format. These images are composed of the following parts:
 a. A header that points to a registry of image headers;
 b. Image headers that point to registries of image metadata;
 c. Image metadata, which includes such detail as width, height, description, colorimetry information, etc.; and
 d. Image data, which may be in two different formats:
  i. Contiguous rows of pixels. Vertically stacking up these rows together will reassemble the image. This format may be used for smaller images. In SVS, these are the label, thumbnail and macro images.
  ii. Tiles, which are listed from top to bottom, left to right. In this case, the image is cut into a regular grid of rectangular tiles, which may be encoded separately. This format may be used for the different magnification levels of the image, in order to allow for partial decoding of these large images. This principle is illustrated by FIG. 1.

The image data in SVS files may be encoded in three different ways. The label image may be encoded using the LZW compression algorithm, while the thumbnail and macro images may be encoded with JPEG. The baseline image and different magnification levels may be encoded in either JPEG or JPEG2000.

Since the magnification levels and tile dimensions exposed by the tile server and those stored in the WSI may differ, decoding a region of the image for the purpose of generating a tile is more complex than simply indexing the right tile at the right magnification level:
 a. First, the procedure may select the WSI level whose magnification power is closest to that requested by the user AND, if possible, of a higher magnification power: selecting a lower magnification power may result in loss of information.
 b. Then, all of the WSI tiles that cover the requested region are blitted to a buffer of dimensions equal to that of the requested region projected to the magnification power of the selected WSI level.
 c. This buffer is then linearly resampled to the dimensions of the requested region. This step may not be necessary if the magnification power of the level requested by the client is equivalent to that of the selected WSI level.

Finally, once a region is decoded and before it can be served to the client, it may need to be encoded back to an image format that the browser will understand. More detail about image formats may be found below. In an exemplary tile server, images are encoded to JPEG with a quality setting of 75.

This series of operations may involve decoding one too many images, potentially resizing an image, and encoding the final result. This can take anywhere between 10 and 100 ms, and sometimes more in pathological cases. The performance of these steps also depends on the encoding, decoding, and resizing algorithms used. In an exemplary embodiment of the tile server, the MozJPEG5 image decoder and encoder may be used, due to its being at least twice as fast as the current best Rust implementation.

Image Formats

There exists a multitude of WSI formats, which use different container formats and compression techniques: SVS (.svs); Philips iSyntax (.isyntax); Hamamatsu (.vms, .vmu, .ndpi); Leica (.scn); MIRAX (.mrxs); Sakura (.svslide); and Other TIFF variants. These formats may be the output of the corresponding manufacturers' scanners. Some slide viewers may store the originals and use vendor frameworks and the OpenSlide open-source library to open and read images whenever the user opens and views a slide. However, this process may have a number of drawbacks.

In order for the frameworks to read a slide, the slide may need to be present on the local FS. Downloading a tile or mounting a remote FS will add latency to the process. Furthermore, since these files are very large, the cost of keeping them in hot storage is uneconomical.

Secondly, these frameworks may each have their own implementations, behaviors, and APIs. This may result in different performance profiles between them. Consequently, the user experience may be different between slide formats, as some will take longer to load than others. It also greatly increases the complexity of the tile server, which may need to call into them all.

Lastly, there is less control over the compression techniques used by the WSI formats. Some file formats use older compression techniques that are likely non-optimal today, therefore taking up more space or using more processing time to decode than is necessary.

Compression Methods

The main compression techniques used by SVS and Philips iSyntax are the Discrete Cosine Transform (DCT) (JPEG) and the Discrete Wavelet Transform (DWT) (JPEG2000). Even though they both support lossless compression (JPEG through the JPEG Lossless extension), they are used in their lossy form.

JPEG2000 is a more recent technique than JPEG, and results in better compression ratios than JPEG at the same image quality level. However, it is more computationally expensive, which makes it less suitable in scenarios that involve repeated encoding and decoding. Furthermore, since its appearance 20 years ago, JPEG2000 has failed to gain widespread adoption, and is only used in rare cases such as histopathology slide storage. Finally, JPEG2000 is not supported natively in browsers, while JPEG is.

Compression Methods

More recent image compression techniques include:
a. WebP, which uses the VP8 codec. While it is not the most performant format today, it is supported by all major browsers except Safari, which may support it in version 14.
b. HEIF, which uses the HEVC codec. Not currently supported in any browser.
c. AVIF, which uses the AV1 codec. Not currently supported in any browser, but with intent to support in Chrome and Firefox.
d. FLIF. Not supported in any browser.
e. JPEG XL. Not finalized, and not supported in any browser.

All of the aforementioned formats may outperform JPEG in the general case, and often may outperform JPEG 2000 as well.

For the present disclosure, JPEG XL may be the most promising image format. Backed by the Joint Photographic Experts Group (JPEG), it promises the following properties:
a. Best-in-class image compression ratios and image quality;
b. Fast encoding and decoding performance thanks to a design adapted for multithreading and Single Instruction Multiple Data (SIMD);
c. Some backwards compatibility with JPEG decoders; and
d. Lossless transcoding of legacy JPEG files.

Furthermore, JPEG XL also may include the Brunsli13 JPEG repacker, which may allow for a decrease in file size while allowing the original JPEG to be recovered byte-by-byte. Considering the amount of legacy JPEG image streams that an exemplary embodiment of the present disclosure stores, adopting such a format may result in significant savings.

As mentioned above, except for WebP and with the exclusion of Safari, currently none of these newer formats are supported natively in browsers. However, this does not necessarily eliminate their use: thanks to Wasm, it may be still possible to decode some of these formats in the browser. Notably, the reference JPEG XL implementation ships with support for WebAssembly.

Contrary to the browser's native JPEG decoder, Wasm implementations may not be capable of taking advantage of multithreading or SIMD, as these features are currently only partially available in browsers. Hence, it is unclear whether these implementations may be able to provide the necessary performance for fast client-side decoding. Nonetheless, since some of these formats are generally faster than the best JPEG decoder available today, it is likely that this may be possible.

Pre-Tiling

The anatomy of a tile request is described above, and it is explained that the faster path occurs when the requested tile had already been generated. If this idea is taken further, and a user expects all tiles to already be generated, the architecture of the tile server may be simplified. In fact, the architecture may be simplified to a point where it becomes a static file server, i.e. a server whose purpose may be to serve content that never changes. Such a server may be highly optimized so that requests are very fast. The architecture of such a server is illustrated in FIG. 8.

FIG. 8 is a workflow illustrating an exemplary embodiment of the server architecture. The workflow may start with a user 801, who may request a file from a server. In step 802, the workflow may include a server determining whether the file exists on the server. When the user requests a tile that does not exist, no corresponding file is found on the server and an error 803 is sent to the client. However, if the file does exist, the server may serve the file in a step 804.

The hot path (e.g., the process between steps 802 and 804) is serving the file directly. However, this case may be undesirable under normal use of the tile server since the client knows exactly which tiles are available.

Such an architecture would still involve the tiles being generated at some point. This may be the responsibility of the slide ingestion pipeline, and would likely occur as soon as the slide becomes available on associated servers. In so doing, it would become available to the user as soon as possible.

While pre-tiling may seem like a suitable solution, it still presents a couple of drawbacks:
a. Pre-tiling implies some added latency between the time the slide arrives on associated servers and the time it is available to the user. However, this may not be an issue in practice since such a process may be continuous and automated, and users might not need the results instantly. Furthermore, it could in theory be mitigated by falling back to the original tile server architecture when tiles are not available yet. Finally, if the process of generating tiles is fast enough, this might only incur a delay of a few dozen seconds.
b. Contrary to on-demand tiling, pre-tiling may imply storing all the generated tiles of a slide, at all times. In practice, this doubles the amount of space that is necessary to store slides, with in turn increases storage costs. A corollary of this is that it also maximizes the processing time necessary to generate tiles.

Viewer Architecture

In some embodiments, the viewer may run in two main loops. One loop is the background loop, which handles image requests, decoding, and loading in graphics memory, as well as cache pruning, or cache sorting, operations. The second loop is the render loop, which might only handle rendering to the display.

During their execution, these two loops may call different components of the viewer. The core computes tile visibility and the draw calls that may be necessary to draw them on the display. The renderer acts as bindings to the underlying graphics implementation, which can be 2D Canvas, WebGL, or any native graphics API. The loader asynchronously loads tiles, either from a remote source (web) or from a local file system (native).

The cache stores tile images and GPU textures, and occasionally prunes, or sorts, itself when its maximum occupancy is reached. A tile stored in the cache may be stored in one of two states: (1) tile request state, or (2) fully loaded state. In the tile request state, the tile may be in the process of being loaded, such as from a tile server or other storage device. In the fully loaded state, the tile image may have been fully loaded. Additionally, for example, if a tile from a previous group has not yet been fully loaded, the viewer may not store tiles from the next group.

Additionally, there may be a third loop that is dependent upon the platform on which the viewer runs: the event loop, which processes user events such as mouse events and keyboard events. In the browser, it may be automatically handled by the JavaScript engine. The event loop is where FOV changes are applied: when the user clicks and drags the display, events are fired, and the application logic updates the FOV accordingly.

Figure 9:
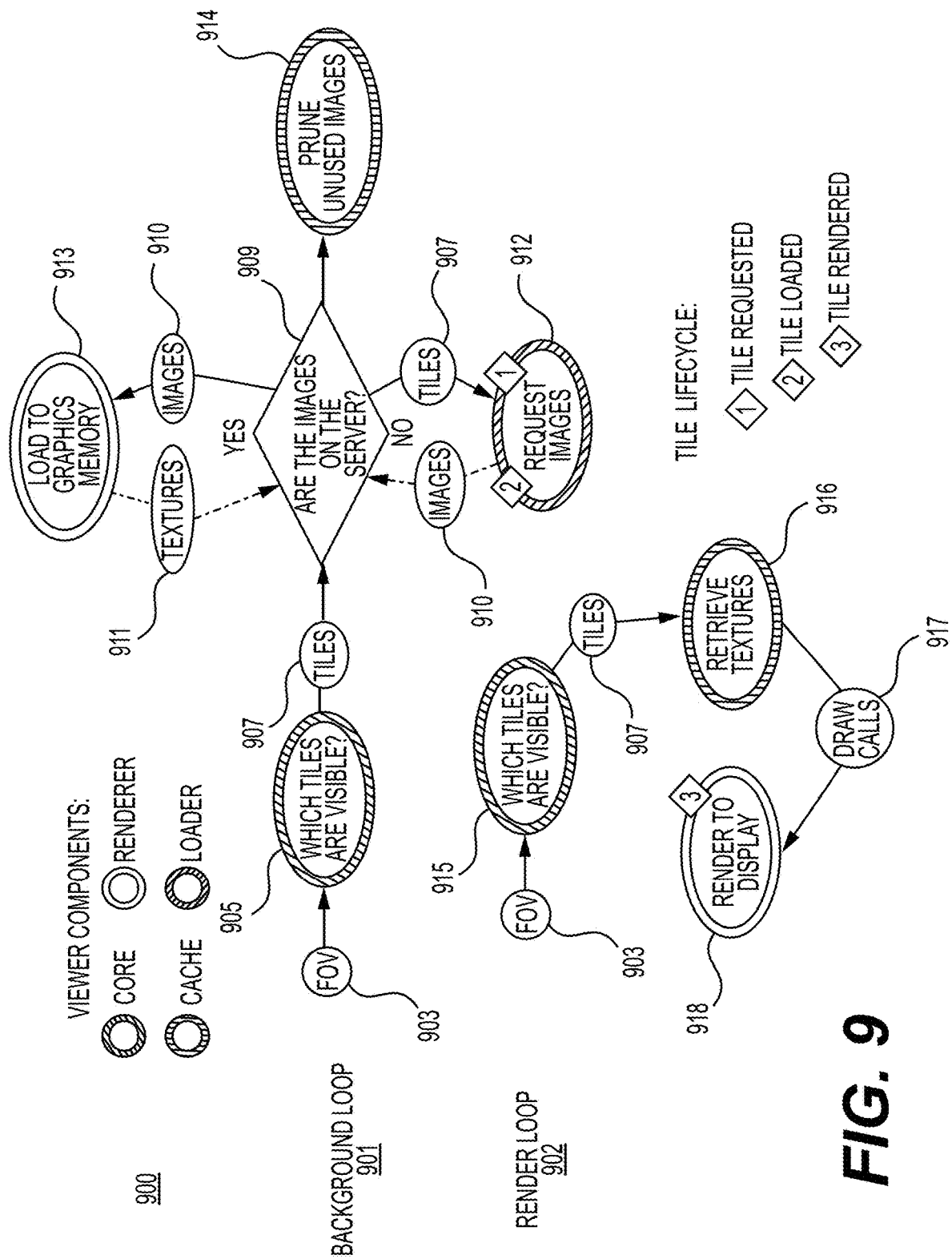
FIG. 9 is a flowchart illustrating the main loops of a viewer architecture, according to an embodiment of the present disclosure.

FIG. 9 is a summary 900 of the flowcharts of both these loops.

Background Loop 901

The background loop 901 may be where most of the background processing happens. It may be scheduled to run any time the process has time to spare before the next frame starts. It may even be scheduled in a background thread. The background loop 901 may proceed as follows:

Given a FOV 903, the background loop 901 may compute the tiles currently visible within it. This may be accomplished by a core processor of the viewer determining, in a step 905, which tiles are visible.

For example, when the viewer's FOV changes, the viewer may load tiles from the cache in groups in the following order of priority:
   a. Tiles within the FOV at a magnification level, which may be equal to or greater than the FOV's magnification factor;
   b. Tiles bordering the FOV at a magnification level, which may be equal or larger than the FOV's magnification factor;
   c. Tiles within the FOV at a higher magnification level; and
   d. Tiles within the FOV at a lower magnification level.

Additionally, when the viewer loads a tile from the cache, if the tile was not previously stored in the cache, the tile may be automatically stored in the cache.

For example, the tile retrieved from the cache may have a magnification level equal to or greater than the FOV's magnification level. However, in some embodiments, this is not always possible because tiles may not be computed for an infinity of arbitrarily large magnification levels. In such situations, for example, when the FOV's magnification factor may be past the largest tile magnification level available, a tile from the largest tile magnification level available may be retrieved from the cache.

The FOV's magnification factor may be a continuous value. For example, the FOV magnification factor may be 0.1, 2.0, or it could be 0.123456 . . . , etc. A tile's or WSI's magnification level may be a set of tiles, where the set of tiles may correspond to a discrete and bounded magnification factor, for example, 1, 2, 4, 8, etc. For example, when the FOV's magnification factor is 2, tiles with magnification levels greater than or equal to 2 may be loaded. However, if no such tiles exist, tiles with the magnification level with the largest magnification factor available may be loaded. Such a process may occur on the tile server and/or the viewer.

If any of the tiles 907 are not found in the cache of the viewer, as may be determined in a step 909, the cache may start asynchronously loading their images. Images may be loaded by a loader of the viewer, which may request images 910 in step 912. The images 910 may be sent back to the cache after the request is made.

If any of these tiles 907 has an image 910 loaded in cache but no associated texture 911, it may start asynchronously uploading the texture 911 to the GPU of the viewer, as shown in step 913.

Once all requests have been made, if necessary, the cache may be pruned to free graphics and system memory of unused tile images and GPU textures in step 914.

Render Loop

The render loop 912 may be responsible for updating the display to reflect the changes to the FOV 903. The render loop 912 may be scheduled to run once per display frame, which would be 60 times per second (60 FPS) on most monitors. The render loop 912 may have a process as follows:

Given a FOV 903, the render loop 912 may compute the tiles currently visible within the FOV 903. The process may include a step 915, where the rendered of the viewer may determine which tiles are visible. If any tiles are not found in the cache, the render loop 912 may instead look for tiles from different magnification levels that cover the tile's surface area.

The renderer may then retrieve textures as needed, as shown in step 916. The render loop may then generate draw calls 917 that describe where to draw the tiles' textures on the display and sends them to the renderer, whose responsibility it is to actually execute them, as shown in step 918.

Rendering Technics

Using generics, the viewer may delegate some or all rendering logic to an external implementation. This may make it possible to quickly add a new graphics implementation, e.g. to support a new platform, without changing any of the existing code.

Historically, the 2D canvas was the first JavaScript graphics API to be supported across all major browsers. This makes it the most portable. However, as its name suggests, it might only support 2D contexts. As such, may not be suitable for a large number of applications. Furthermore, as a high level abstraction, it may hide much of the complexity of graphics rendering at the cost of performance and customizability. Since the viewer is, in some embodiments, a 2D application, the canvas may be particularly well-suited to render it.

WebGL is an implementation of the OpenGL ES 2.0 standard, designed to run in a browser context. It exposes a JavaScript API for rendering 3D graphics, which also makes it suitable for 2D graphics. It is a lower level API than the canvas, with better control over how operations are composed and how memory is managed. As a thin layer over OpenGL, WebGL has the advantage of being hardware accelerated on most platforms, which makes it generally more performant than the canvas API.

Similarly to OpenGL, WebGL programs are a composition of JavaScript code that schedules operations, and shaders written in OpenGL ES Shading Language (GLSL ES), which are executed directly on the user's GPU. The WebGL backend is comparatively much more complex than the canvas implementation. However, the many advantages WebGL offers over the canvas alternative make it a better choice for certain circumstances. As previously mentioned, WebGL is more performant and more memory-efficient than the canvas API. WebGL supports sub-pixel rendering out-of-the-box, while canvas implementations' support differs across browsers. Because of floating point precision issues, this may cause visible tile seams when compositing tiles next to each other, and may require some more logic on the part of the renderer to handle these special cases. The WebGL API maps almost 1:1 to OpenGL APIs, which means that implementations can be shared between a native context and a browser context. Further, shaders provide a very performant way to add post-processing and advanced compositing to images, which is a fundamental feature of an image viewer.

In order to support the largest browser version area, a frequent pattern in the web development world may default to a WebGL implementation, and fallback to a canvas implementation if WebGL is not supported by the current browser. However, this may involve using only the subset of features from WebGL that canvas supports, which may not work if a program features complex shader code.

WebGL 2.0 is a new specification based on the OpenGL ES 3.0 standard. However, it is not supported by all major browsers, with Safari as a notable holdout.

WebGPU is an upcoming API that exposes even lower-level graphics capabilities to web applications. It is based in parts on the Vulkan specification, with the goal of efficiently mapping to the Direct3D (Windows) and Metal APIs as well.

While WebGPU is not available out-of-the-box on most browsers today, it is still possible to enable it in the experimental settings of the latest browsers. WebGPU represents a promising development in the graphics programming world: the promise of a unified API that can target any graphics backend and thus work seamlessly across different platforms.

The present disclosure includes an embodiment with implementation of a WebGPU backend using the wgpu5 Rust crate. For now, this backend only powers the native version of the viewer. With one implementation, the native viewer may be able to run on Linux, Windows, and macOS, with the promise of being able to target OpenGL, WebGL, and future WebGPU implementations in the browser.

As it targets an even lower-level API, the disclosed WebGPU implementation is more complex than either the canvas or WebGL implementations. However, the WebGPU API is well designed, and the abstractions provided by the wgpu crate may make it relatively easy to use. In the coming years, WebGPU development may likely become even easier, with better tooling and support becoming available.

Optimization Techniques

Performance may be a key component and serves to guide technological choices in an exemplary embodiment of a slide viewer. However, because of product constraints, some of these choices are already made. Perhaps the most important of them is that the viewer may be a web application.

If the viewer is a web application, the number of technologies available for use with the viewer may be restricted. However, in part due to WebAssembly, WebGL, and potentially WebGPU, it remains possible to write very performant graphical web applications. Nonetheless, some parts of these applications must still communicate over the network, and are thus constrained by both the browser's network stack and the client's internet connection. Web applications may be further constrained by the need to fit in the allocated browser's memory, with access possibly only to Web APIs.

Cache Heuristics

A browser, and in a wider sense a user's computer, may have a limited amount of memory available. As such, it may not be possible to keep all images that will be loaded as part of a user's session in memory, as it would be akin to storing the whole slide image on the user's device. These images may be gigabytes-large encoded, and dozens of gigabytes-large decoded. As such, as mentioned above, it may be necessary to implement cache-pruning, or cache sorting, heuristics in order to keep the occupancy of the cache at a manageable size.

Pruning or sorting the cache may refers to an operation of determining the priority of each tile currently stored in the cache and pruning the cache, if necessary. The sorting of the cache may be triggered when the cache is over maximum occupancy. For example, the viewer may determine that maximum capacity is reached when the cache is completely full. Alternatively, the viewer may determine that the maximum occupancy is a particular level of capacity of the cache. When the cache is at and/or over maximum occupancy, the contents of the cache may be examined to determine which tiles have the lowest priority. The tiles that have the lowest priority may be removed from the cache until the cache is at or below the maximum occupancy.

In one embodiment, the order of tile priority in the cache may include:
  a. Tiles within the FOV at a magnification level, which may be equal to or greater than the FOV's magnification factor;
  b. Tiles bordering the FOV at a magnification level, which may be equal or larger than the FOV's magnification factor;
  c. Tiles within the FOV at a higher magnification level;
  d. Tiles within the FOV at a lower magnification level; and
  e. all other tiles.

Figure 10A:
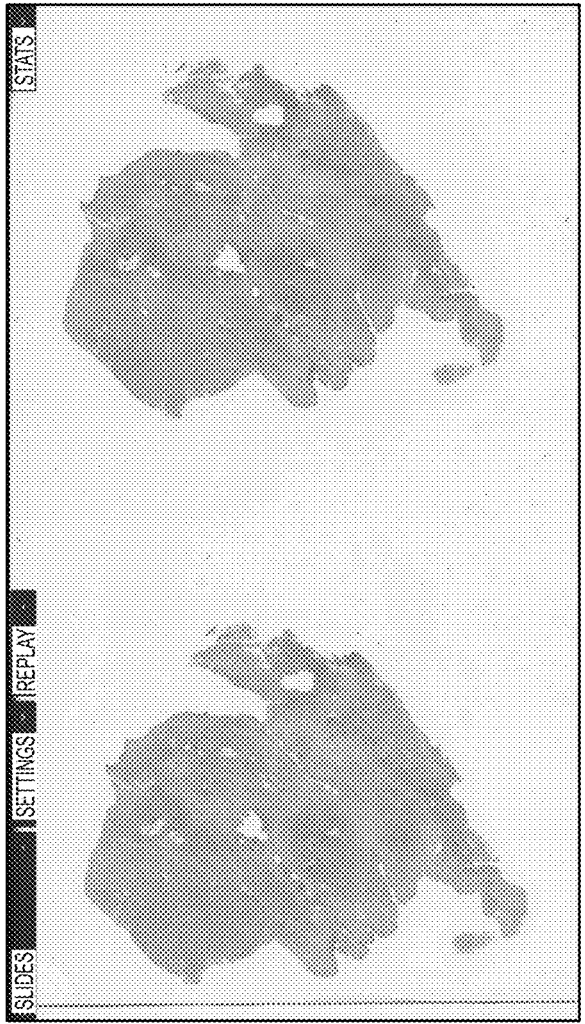
FIG. 10A depicts a first look at a slide in a viewer, according to an embodiment of the present disclosure.
Figure 10B:
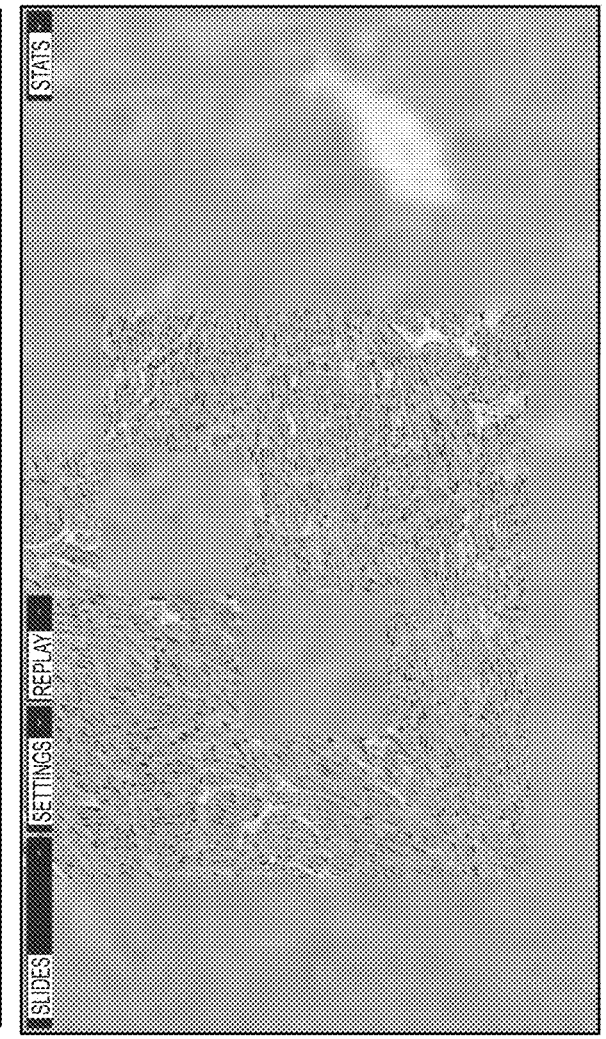
FIG. 10B depicts a loading Field of View in a viewer, according to an embodiment of the present disclosure.

In another embodiment, during each cache cycle, tiles may be sorted in three categories:
  a. Tiles that are currently directly needed for display. Looking back at FIG. 2, these are the tiles 11 marked as "active". These active tiles 11 may also be seen in FIG. 11.
  b. As shown in FIG. 10A, when a slide image is first loaded, it may be displayed in its entirety. During this first display, a set of tiles may be loaded at a low magnification level. These tiles may be used for interpolation purposes, when tiles at the correct magnification level are being loaded and there may be a need to display something in their stead. FIG. 10B showcases such an example, where a low magnification tile is interpolated to display instead of a high magnification tile while the latter is loading.
  c. Other tiles are sorted into four subcategories, by decreasing order of importance:
     i. Tiles that are directly bordering the FOV;
     ii. Tiles that are within the FOV, but at greater magnification levels;
     iii. Tiles that are within the FOV, but at lower magnification levels;
     iv. All other tiles.

Tiles that belong in categories 1 and 2 may be always kept in memory, since they are either needed instantly, or always may be needed eventually for interpolation purposes. Tiles that belong in category 3 may only be kept up to a maximum occupancy, after which tiles that are considered to be low-priority start to be pruned.

Furthermore, these heuristics apply to more than just decoded images. Indeed, image requests will follow the same heuristics, with the added constraint that no request from category 3 can run at the same time than requests from categories 1 and 2. Pending requests for low-priority tiles are cancelled when requests for high-priority tiles come in. This ensures that requests for necessary tiles might be always prioritized.

Tile Preloading

FIG. 2 demonstrates the active tiles 11 the viewer may load in order to render a specific FOV 12. However, an exemplary embodiment may start loading tiles that the viewer predicts the user might visit next.

Figure 11:
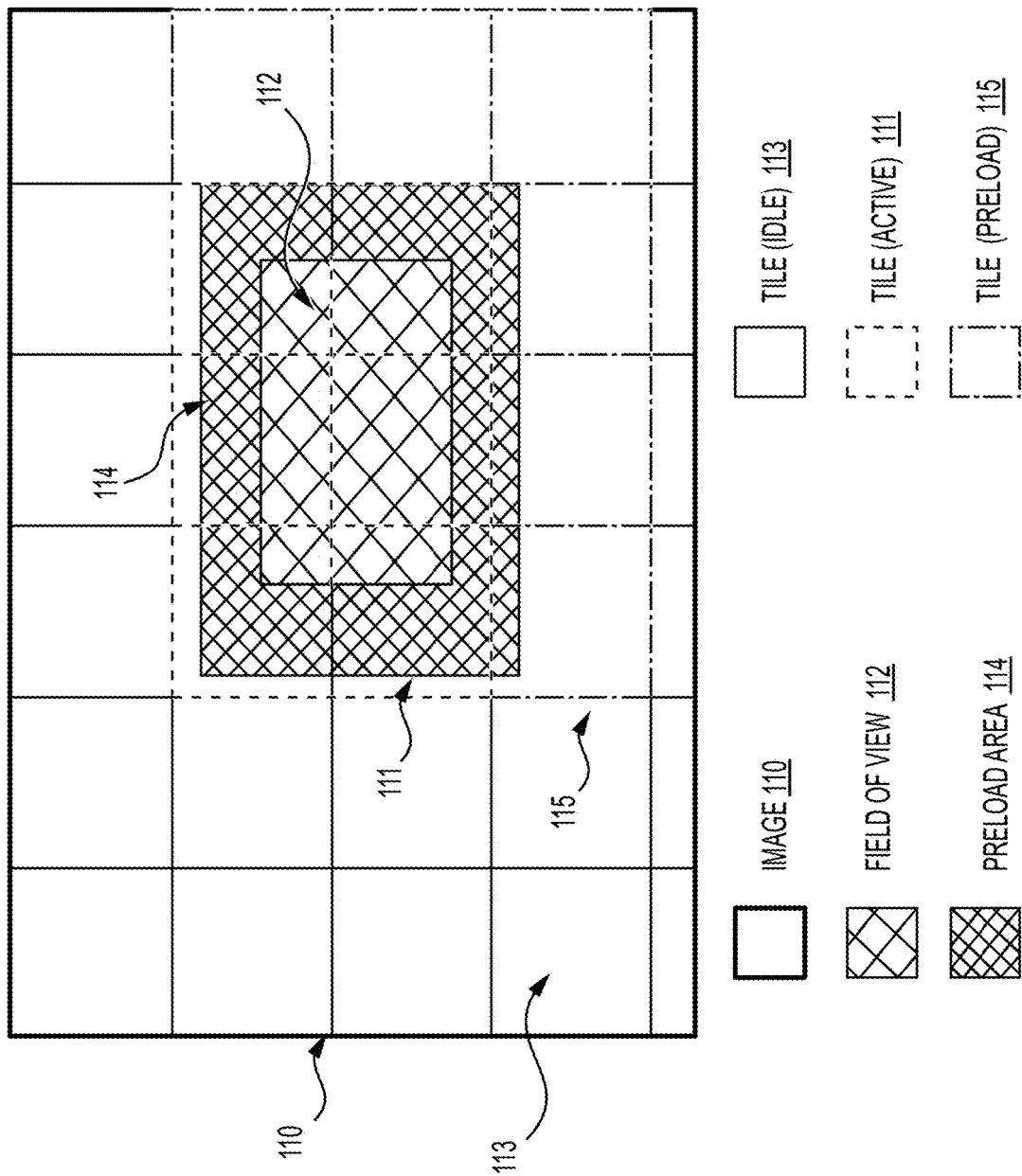
FIG. 11 depicts a Field of View with preloading tiles in an exemplary viewer, according to an embodiment of the present disclosure.

FIG. 11 showcases an example of this behavior in action. Since the slide viewer may expect the user to pan the FOV 12 at some point, it may increase the size of it to form a "preload area", such as preload area 112. Tiles 111 in preload area 112 may be loaded in the background so that they may become instantly available when the user needs them.

As described above, these tiles 111 may be considered a part of subcategory (c)(i). As such, requesting these tiles 111 may not slow down other tile requests, and may not come at the cost of pruning other more important tiles.

Despite the potential gains in user experience, this approach may also have drawbacks. One such drawback may be preemptively loading a larger region of the image, meaning that more requests are made to the tile server, and some of these requests will be wasted. As such the data transfer costs with preloading tiles are higher than without. Another drawback is that preloading too large an area may put a strain on both the user and the server. In practice, this may cause stutter on the frontend, and increased latency on the backend. However, this may be alleviated through the use of a Content Delivery Network (CDN) on the server-side, and proper request scheduling on the client-side.

Parallel Tile Loading and Decoding

Figure 12:
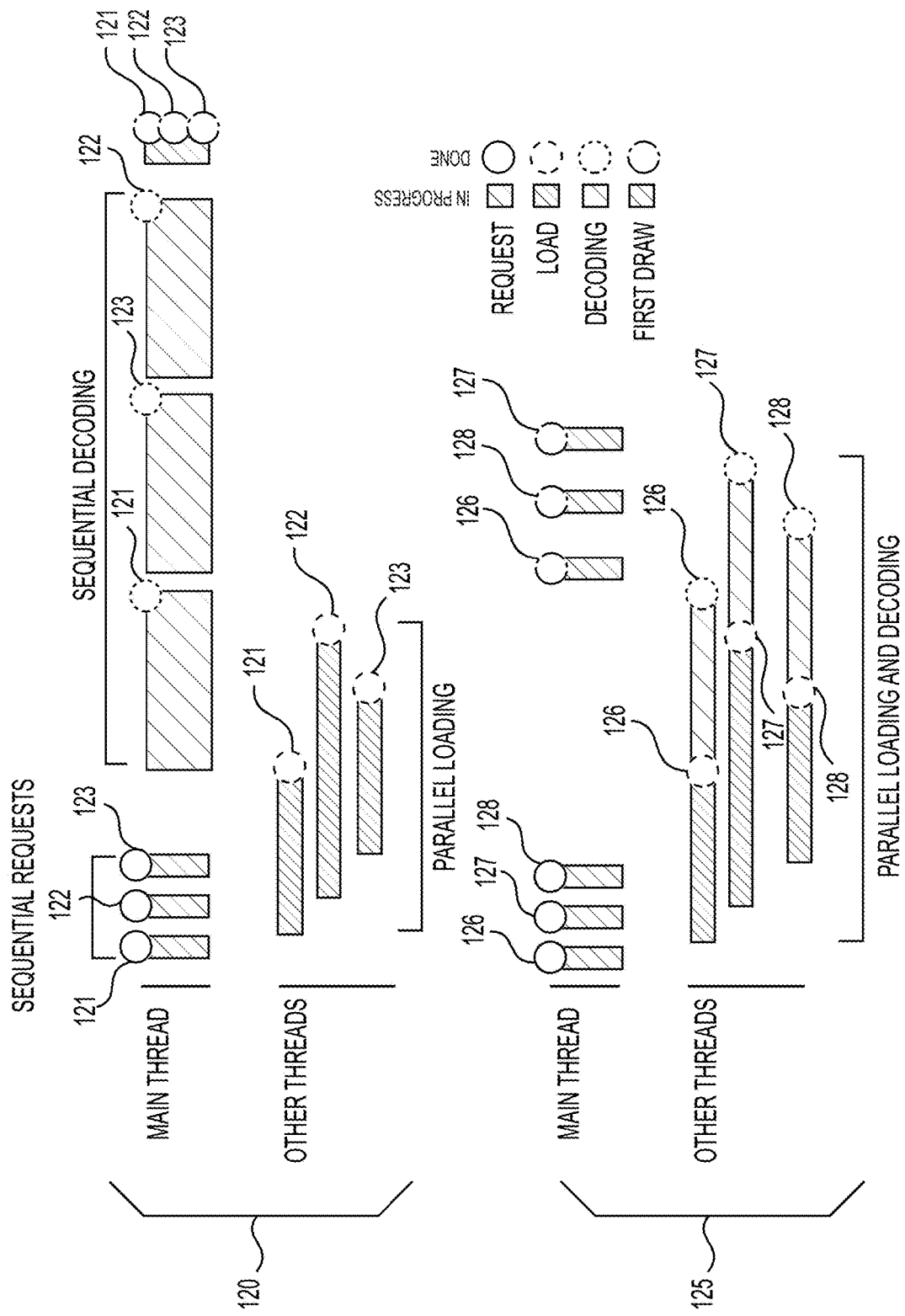
FIG. 12 illustrates a timing breakdown of an exemplary tile decoding within a viewer, according to an embodiment of the present disclosure.

In modern browsers, while resource loading happens asynchronously in the background, image decoding may happen in a main thread. As such, decoding a large number of images may lead to increased latency, delay the render loop, and, consequently, cause a drop in FPS. FIG. 12 shows an exemplary timeline of requesting, loading, and decoding tiles in a sequential manner with sequential requests 121, 122, and 123 in the top half 120, and sequential requests 126, 127, and 128 in the bottom half 125. If image decoding only happens in the main thread, it may be purely sequential, and it may become necessary to wait for decoding to complete before the render loop is able to be executed.

In the top half 120 of FIG. 12, sequential requests 121, 122, and 123 may be within a main thread or another threads. The sequential requests 121, 122, and 123 may be decoded and stored sequentially, or may be decoded in another order and stored sequentially as a part of the main thread. The parallel loading of the sequential requests 121, 122, and 123 may involve varying amounts of time, but may start with the sequential order.

This is similar to the bottom half 125 of FIG. 12, wherein sequential requests 126, 127, and 128 may exist in the main thread or within other threads. The spacing between the sequential requests 126, 127, and 128 may vary within the main thread. Within the other thread, parallel loading and decoding times for the sequential requests may also vary, and may be completed within the same step of the thread. Additional detail regarding sequential requests is provided below.

WebWorkers are a recent addition to the web APIs family. WebWorkers may leverage the multi-threading capabilities of modern processors to execute JavaScript and Wasm code in parallel to the main thread. JavaScript is, by nature, single-threaded, which means that it might only run on a single thread. In order to allow for parallel computing in JavaScript, it may be necessary to use multi-processing and message-passing. This is the basic concept of a WebWorker: it may run in an independent JavaScript context, and may pass data back and forth to the main thread through channels.

Using WebWorkers, it may become possible to decode images off the main thread. Offloading work to different threads may ensure that the main thread is free to execute its more important responsibilities, including event processing and rendering. FIG. 12 shows that by deferring decoding to different threads, faster rendering with higher frequency is achieved.

This technique can also be used for rendering thanks to the recent addition of the OffscreenCanvas API. However, rendering currently may not be a bottleneck for the viewer, so it was not implemented.

Finally, it must be noted that while JavaScript cannot have threads, it may still be possible in the future to share memory directly thanks to the SharedArrayBuffer API. Furthermore, the Wasm specification supports a threading model, and Wasm threads may already be available in Chrome and Firefox.

Example Embodiment

An example embodiment may include a user adjusting the FOV so that the FOV covers 4 tiles that are indexed by their coordinates in a grid, such as (4, 4), (5, 4), (4, 5), (5, 5). The viewer may then load tiles (4, 4), (5, 4), (4, 5), (5, 5), which may all be located within the FOV. Tiles (4, 4) and (5, 4) may already be stored by the cache in the fully loaded state. Tiles (4, 5) and (5, 5) may not be stored in the cache, which may result in such tiles being stored in the tile request state. The tile request state may be stored in the viewer or in the tile server. For example, the viewer may send a tile request to the tile server to load tiles (4, 5) and (5, 5). The tile request may include a tile identifier, such as the specific FOV coordinates or a different unique identifier. The tile server may transfer data to the viewer. Such data may include complete tile information in order for the tiles to be fully loaded. The viewer may move tiles (4, 5) and (5, 5) to the fully loaded state. Now that all of the tiles are in the fully loaded state, the viewer may proceed to load bordering tiles (3, 4), (4, 3), etc, where the previously described method may repeat for the bordering tiles and subsequent groups of tiles. Additionally, the user may adjust the FOV again and the viewer may load tiles from the cache for the new FOV.

The cache may be at maximum occupancy from the previous method. For example, all of the tiles that were loaded from the method may have filled the cache to maximum occupancy. Using the new (or current) FOV, the cache may sort the stored tiles and remove low-priority tiles until the cache is no longer at maximum capacity. Such a sorting process may also occur at any time in the process.

Furthermore, the viewer may render the tiles at any point during the above-described process. The viewer may render the tiles in the fully loaded state to a display or a storage device. This may be the rendering loop, where the execution of the rendering loop may be independent to the background loop method.

Work Scheduling

As mentioned above, the background loop may need to be executed whenever the current process has time to spare. On the web viewer, it may be scheduled to run just before the render loop. While this works, it may not be optimal, as it may cause the render loop to miss a frame if the background loop takes too long.

An early example of work scheduling is the experimental requestIdleCallback API. Using this API, the background loop may be called whenever the browser has an idle period. Furthermore, since it executes multiple small units of work, the background loop is by nature pausable. Its execution may be temporarily paused if a timeout is reached, then resumed on the next frame. Hence, in the near future, its model may be able to take advantage of the new browser scheduling APIs.

Performance Metrics

The tracer component of the instrumentation framework is responsible for timing the duration between the instant the first request is made for a tile, the instant the tile is loaded from the server, and the instant it is finally rendered on screen. These events are illustrated in FIG. 9. Since loading and rendering may happen in different components of the viewer, the tracer is wide-reaching across the application. The tracer may achieve this by wrapping the different components it needs to measure, which all expose a generic API. As such, to disable the tracer, the user may need only to remove these wrappers.

An important metric gathered by the instrumentation framework is the FOV completion time. The FOV completion time may measure the time elapsed between the instant a user interaction causes a change in FOV, and the instant the new FOV is fully rendered on screen.

Some interactions may result in instant FOV completion, since the tiles necessary to display the FOV may already be in cache. As such, the framework may only consider FOV completion events when an incomplete FOV was presented to the user for at least one frame. An incomplete FOV is one where a tile texture has yet to load, and may be replaced with an interpolated version of a lower magnification tile in cache.

The FOV completion time is also called the turnaround time. The Food and Drug Administration (FDA) has specific guidelines regarding the turnaround time allowance of a viewer application for different user interactions. The exemplary embodiment only uses a fraction of the FDA turnaround timeline guideline.

While the FOV completion time is a purely quantitative metric, a more qualitative metric of user experience is measuring the average percentage of completion of the FOV over a user's session. The purpose of this metric is to quantify the amount of time the user spent on an incomplete FOV, and the amount of partial information displayed on the screen at any time.

For every frame rendered on screen, the tracer may look at the tile draw calls to see which draw calls refer to textures that are at a lower magnification level than the current FOV magnification level. Since a complete FOV may only display textures at a magnification level equal or higher than its own, a frame containing a lower magnification texture will necessarily be incomplete. The area covered by these draw calls may be measured and divided by the area of the FOV, indicating the percentage of incompletion (and, reversely, completion) of the FOV. The algorithm may be slightly more complex, since it is possible for a higher magnification texture to be overlaid upon a lower magnification texture: while the exact texture necessary to render a tile might not yet be available, it is possible that a higher magnification subtile and a lower magnification supertile are available in cache.

Finally, the simplest metric to measure is the time it takes to load and render a single tile. This metric may be mostly indicative of the performance of the tile server, but may also reveal issues with the tile loading and rendering pipeline.

For instance, using the HTTP/1.1 protocol, most browsers will limit the number of requests that can be made in parallel to a specific host. In Chrome, that number may be 6. Even with a fast tile server, such a limitation may artificially inflate the tile loading time when loading more than 6 tiles in parallel, as later requests will be queued by the browser. In an exemplary embodiment described herein, tile servers use the HTTP/2.0 protocol exclusively, which may not suffer from these limitations.

Recording and Replaying User Sessions

Gathering enough data to compile meaningful comparison benchmarks is always a challenge. As such, a need exists for a way to quickly and efficiently generate realistic usage data.

One approach to comparing one solution to another may be to manually replay the steps of a normal user session with tracing enabled, to see which solution appeared to have the best performance after looking at samples. This approach may have several drawbacks, including additional time taken by a user as it is completely manual. Further, the method may not be scientific and may not gather enough samples to show any significant difference.

In order to avoid these drawbacks, a session recorder and player may be used. User interactions may be recorded alongside the instant they occurred, so they may be replayed later at the same speed. One major difference between the original user session and the replayed session may be that the session player does not wait any further between user interactions once it notices that the FOV has fully resolved. This may mean that replayed sessions may generally be faster than the original. It also may mean that they will be more taxing on the part of the viewer, since the events will occur at a faster rate on average. As such, it is not representative of a completely realistic usage scenario, but, at the worst, of one more stressing to the system.

Benchmarks

The following benchmarks were captured on a computer with the following specifications:

Model: MacBook Pro, 13-inch, 2019

CPU 2.8 GHz Quad-Core Intel Core i7

Graphics Intel Iris Plus Graphics 655 (integrated)

Graphics Memory 1536 MB

Memory 16 GB 2133 MHz LPDDR3

Internet Bandwidth 300 Mbps

On the server-side, instances are running on AWS EC2 instances of type m5a.4×large with the following specifications:

CPU 2.5 GHz AMD EPYC 7571, 16 threads

Memory 64 GB

The benchmarks were captured on a set of 10 SVS slides from different tissues. All of the slides were scanned with 40× magnification power. The below chart details tissue types, slide size and resolution.

| Tissue Type | Size (GB) | Width | Height |
| --- | --- | --- | --- |
| Adrenal | 2.1 | 129 480 | 95 624 |
| Bladder | 2.4 | 141 432 | 78 605 |
| Brain, cerebellum | 3.1 | 129 480 | 82 966 |
| Brain, cortex | 3.0 | 99 600 | 92 207 |
| Colon | 2.6 | 111 552 | 96 671 |
| Heart | 2.3 | 123 504 | 81 983 |
| Kidney | 2.8 | 141 432 | 67 614 |
| Liver | 3.1 | 113 544 | 82 680 |
| Lung | 1.2 | 131 472 | 71 639 |
| Lymph Node | 1.4 | 89 640 | 79 414 |

For benchmarking the exemplary viewer/tile server combo, the process is divided into two parts. First, a series of user actions is recorded, which are saved as a user session for later playback. Then, once user sessions are generated for all slides in the dataset, the user sessions are replayed.

The process for recording a user session may include the following steps:

a. Clicking on a slide on the slide tray to open it and start recording.

b. Navigating the slide using a series of zooms and pans for 3 minutes.

c. Saving the user session.

d. Repeating the process for the next slide.

The process for generating benchmarks may include the following steps:
 a. Clear all previously generated tiles.
 b. Configure the viewer to the desired settings to benchmark.
 c. Select the user sessions to replay.
 d. The viewer may automatically replay the selected sessions a number of times and save the result to disk.

FOV Completion

Zoom actions may be on average slower to complete than panning actions because they may cause a full invalidation of the FOV: since the viewer is transitioning from one magnification level to another, it cannot reuse tiles that were previously displayed. This contrasts with pan actions, which may still be able to reuse some of these tiles at the periphery of the new FOV.

Even though the following configurations may follow the exact same series of actions, the number of collected samples may vary greatly between them. Ultimately, the number of samples indicates the number of actions that resulted in the user being presented with an incomplete FOV. As such, a smaller number of samples may indicate that a smaller percentage of actions did so. This effect may be particularly visible for the tile preloading configurations as described above, and can be explained in a number of ways. When FOV completion times are very fast, completion events may happen multiple times as the user is panning or zooming. When they are slower, they may only happen once the user is done with these actions. Configurations that require displaying fewer incomplete FOVs may in turn have fewer samples of FOV completion events.

Figure 13A:
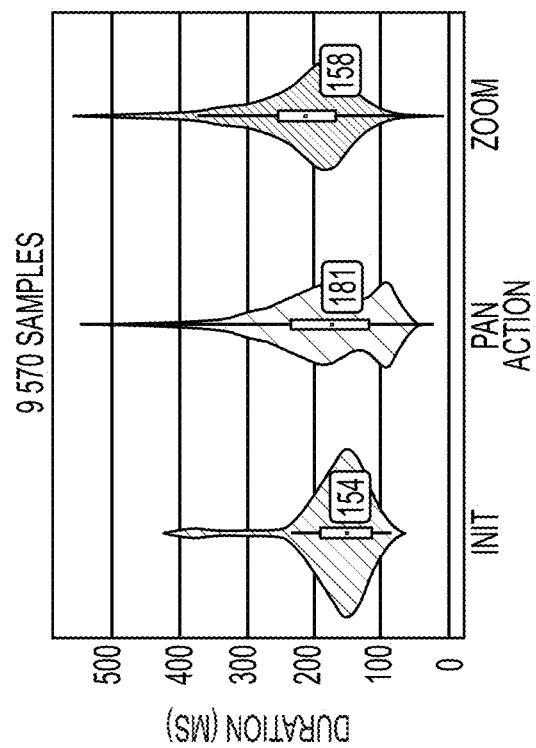
FIG. 13A illustrates a Field of View (FOV) completion for an exemplary embodiment with dynamic tiling, according to an embodiment of the present disclosure.

As shown in FIG. 13A, an exemplary viewer may be configured to never use a tile cache, and instead always generate tiles on-demand. This may be the case for a dynamic tiling benchmark.

Figure 13B:
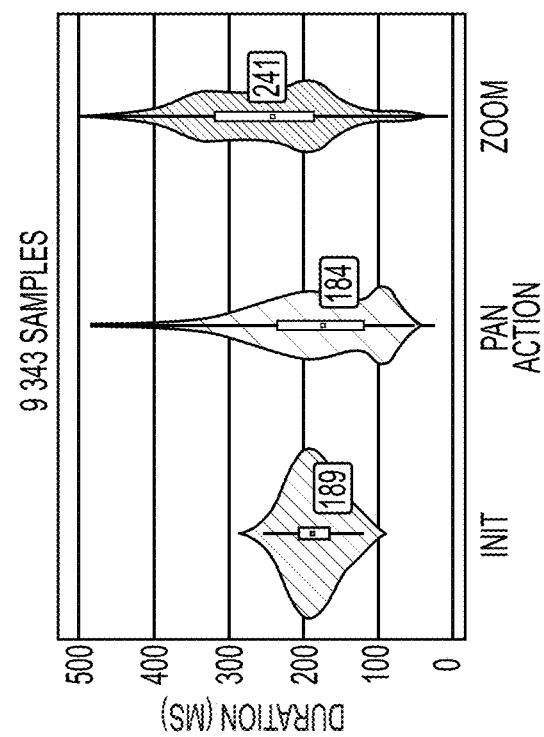
FIG. 13B illustrates a FOV completion for an exemplary embodiment with static tiling, according to an embodiment of the present disclosure.

An exemplary viewer configured for a static tiling benchmark is illustrated in FIG. 13B. For the static tiling benchmark, all of the tiles needed by the viewer were generated ahead of time and streamed from S3 through the tile server. All of the following benchmarks will also use static tiling, as it may be considered to be the most realistic approach moving forward.

The preloading benchmark adds tile preloading to the mix, with four different configurations for the preload offset. The preload offset may be expressed as a factor of the configured tile size. For instance, if the tile size is 512×512 and the preload offset is configured to 0.5, the actual preload offset in pixels may be 512×0.5=256 pixels.

| Configuration | Preload Offset |
|---|---|
| Preload, 1 | 0.5 |
| Preload, 2 | 1.0 |
| Preload, 3 | 1.5 |
| Preload, 4 | 2.0 |

Figure 14:
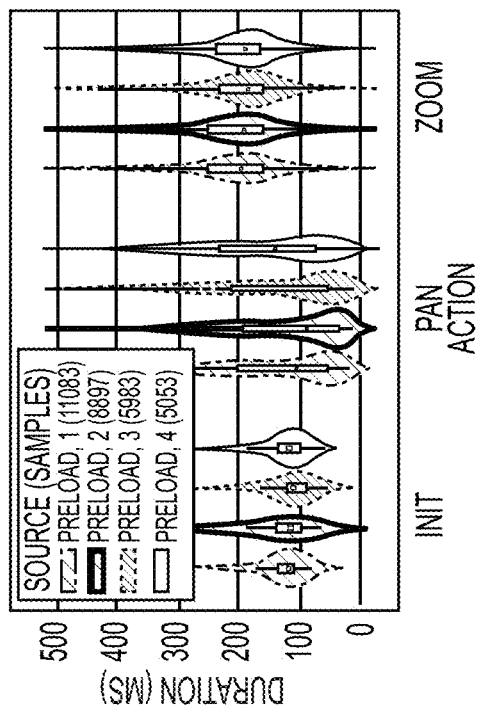
FIG. 14 illustrates a FOV completion for an exemplary embodiment with tile preloading, according to an embodiment of the present disclosure.

FIG. 14 shows that the value of the preload offset may directly affect the FOV completion latency. Furthermore, the preload offset may invalidate the intuition that a greater preload offset necessarily involves faster completion times. This may be explained in a number of ways. A larger preload offset may ultimately require loading more tiles. The number of tiles to load may increase quadratically with the preload offset, which can result in performance issues with large numbers. Furthermore, loading a large number of tiles at the same time may cause strain on the tile server and add to the latency of requests. In the exemplary embodiment, all preload tiles may have the same priority. This may mean that for greater preload offset values, some tiles that are farther from the FOV and thus less likely to be needed may resolve before closer tiles. Finally, the actions in the benchmarks may be run in very quick succession without waiting between FOV completion events. This is a pathological case for tile preloading, which may expect the user to wait at least half a second between actions. During this time, most if not all preload tiles should be properly loaded.

The slow internet connection benchmark may artificially restrict the internet bandwidth to 10 Mbps to simulate slower connections.

Figure 15A:
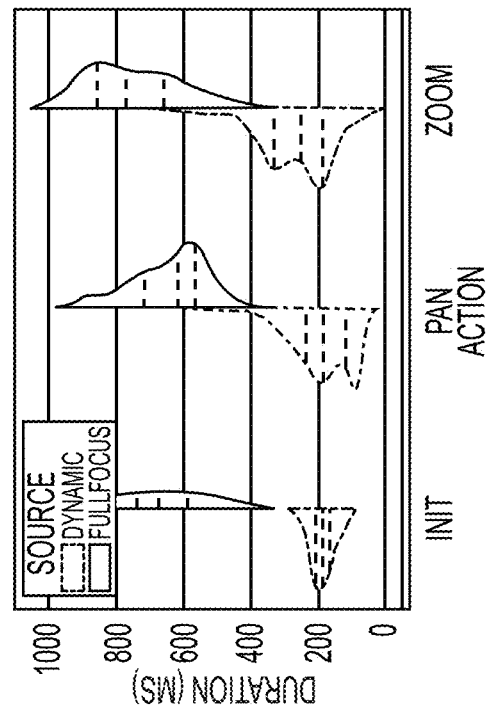
FIG. 15A-15F illustrate different FOV completions for an exemplary embodiment, according to an embodiment of the present disclosure.

FIG. 15A is a comparison of the performance of a known slide viewer vs. the exemplary embodiment with dynamic tiling. The results may show that the exemplary embodiment is almost always, if not always, faster than the known side viewer in the loading of FOVs.

Figure 15B:
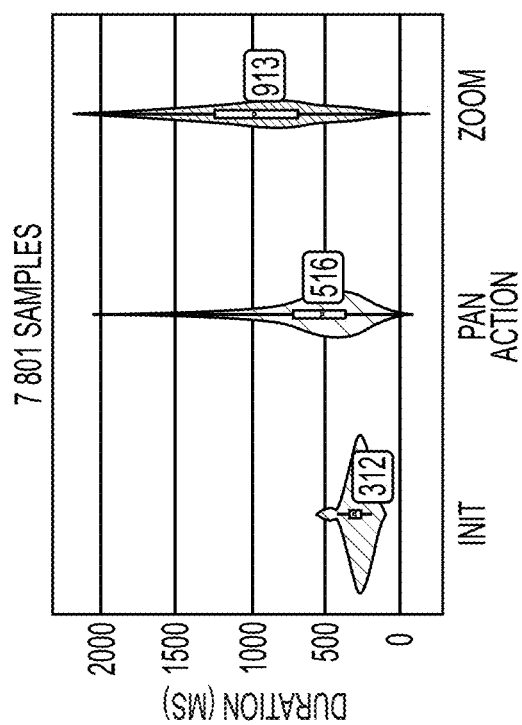
Figure 15D:
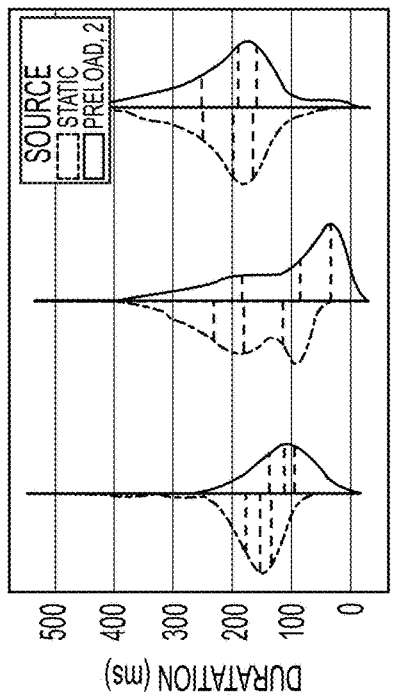

FIG. 15B is a comparison of the performance of an embodiment with dynamic tiling vs. static tiling. The difference may be noticeable in events that require a full invalidation of the display (e.g., initial load and zooming). On the other hand, events that require a partial invalidation of the display (panning) may have little to no discernible difference. This may be explained by the difference in strain these events put on the server: fully invalidating the display may require loading more tiles in parallel than a partial invalidation, and in turn may cause latency spikes.

The current static tiling implementation may not be perfect, as it may require the tile server to act as a proxy between the backing store (AWS S3), and the client (browser). This may add some latency to all requests. Ways of eliminating this latency may include serving tiles directly from the backing store; and/or serving tiles through the AWS Content Delivery Network (CDN), CloudFront. CDNs may be optimized for serving static content, and may greatly improve latency for content that is frequently queried by physically moving the corresponding data to a server that is closer to the client.

These approaches may require partially moving the authentication logic from the tile server (which, at this point, is more of an authentication provider) to the service with which the client will ultimately communicate (e.g., S3 or CloudFront).

Figure 15F:
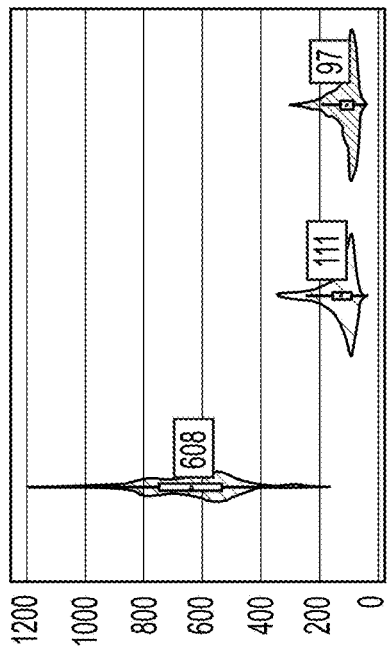
Figure 15C:
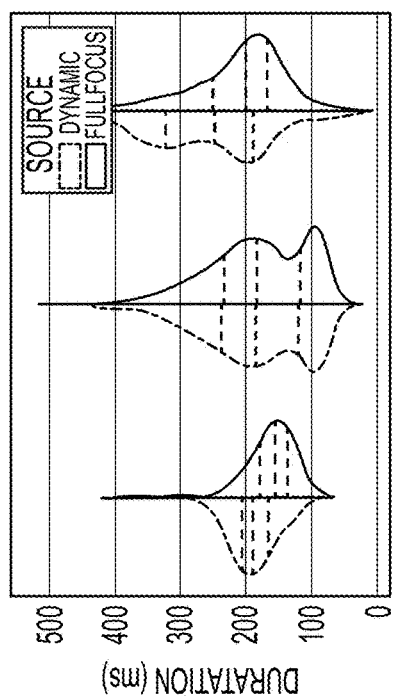

FIG. 15C is a comparison of the performance of an exemplary embodiment with preloading disabled and enabled with a preloading offset of 1, where benchmarks from the above explanation have been shown to strike a compromise between latency and number of tiles loaded. In this configuration, a preloading offset of 1 means adding a preload border of 512×512 around FOVs.

As expected, since the current implementation of preloading may only operate on bordering tiles at the same magnification level, the performance of zoom actions is almost unchanged. However, it may be seen that preloading considerably speeds up panning operations. The difference in latency for the initial loads may only be explained by the small number of samples for these events.

Figure 15E:
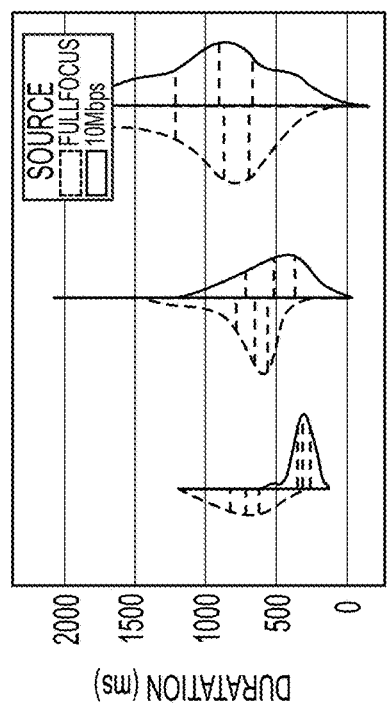

Finally, to further illustrate that the exemplary embodiment may be considerably faster than a known slide viewer, FIG. 15E shows a comparison between a known slide viewer running on a 300 Mbps connection and the exemplary embodiment running on a 10 Mbps connection. The exemplary embodiment is faster on both the initial load and panning actions, but does just as well as the known slide viewer on zooming actions. As explained before, these actions may require loading in many more tiles, which saturates the limited bandwidth.

The time it takes to load tiles is an important factor for the perceived performance of a viewer. As demonstrated in FIG. 15F, the exemplary embodiment tile server implementation may be capable of serving tiles much faster than the known tile server, which may result in a lesser loading time for the user. The difference is not so stark between the dynamic tile server, which generates tiles on-demand, and the static tile server, for which all tiles have already been pre-generated.

When deciding on which configuration to adopt, the main compromise that arises is that of quality of user experience vs. cost of maintenance.

While the quality of user experience may be dependent upon more quantitative metrics such as the average tile loading time, such metrics do not tell the whole story. In order to obtain a more representative metric, the exemplary embodiment may use the percentage of time that the user is presented with an incomplete FOV during a user session. This metric is the Average FOV Completion and is further described above. On the other hand, the principal factor of maintenance cost on the part of the viewer is the average number of tiles loaded during a session. Loading a tile has both a cost in processing power and data egress.

The table below is a breakdown of these two metrics for the different tested configurations.

| Configuration | FOV Completion | Tiles Requested | Tiles Loaded |
|---|---|---|---|
| FullFocus | 0.7909 | 707.1 | 707.1 |
| Dynamic | 0.9952 | 2706.9 | 2222.9 |
| Static | 0.9953 | 2704.0 | 2247.8 |
| Preload, 1 | 0.9963 | 2849.3 | 2514.2 |
| Preload, 2 | 0.9961 | 3262.2 | 2834.5 |
| Preload, 3 | 0.9963 | 3739.8 | 3186.5 |
| Preload, 4 | 0.9961 | 4044.1 | 3338.2 |
| 10 Mbps | 0.9943 | 2717.9 | 2161.4 |

Intuition would have that the higher the preload offset setting, the more tiles would eventually be loaded. This is not necessarily the case, since the viewer may automatically cancel pending tile requests when they prove not necessary any longer. This may be why the Tiles Requested and Tiles Leaded values differ for the exemplary embodiment of the slide viewer. This effect may be particularly visible when preloading tiles.

Similarly, since the played user sessions are the same, and no tiles are loaded other than absolutely necessary, it may be expected that the Tiles Requested value would be equal between the dynamic, static, and 10 Mbps configurations of the exemplary embodiment. However, since the browser's scheduling APIs may not be fully deterministic, slight variations occur between different runs of the same session. The background loop, which is responsible for making tile requests, may run at different times, and capture different FOVs. This effect is small enough that it may be ignored. With these points in mind, the exemplary embodiment may offer a much smoother user experience, even at seemingly comparable data egress cost.

Streaming Viewer

Instead of having a user render a slide viewer directly, in a streaming viewer that responsibility is transferred to the service, which sends back a video stream for a user to display. The implementation may make extensive use of a streamer library, such as GStreamer and its WebRTC support, to enable live video encoding and streaming to a user with minimal latency (<100 ms). This may be in part thanks to the support of new video codecs such as VP8 and VP9.

Figure 16:
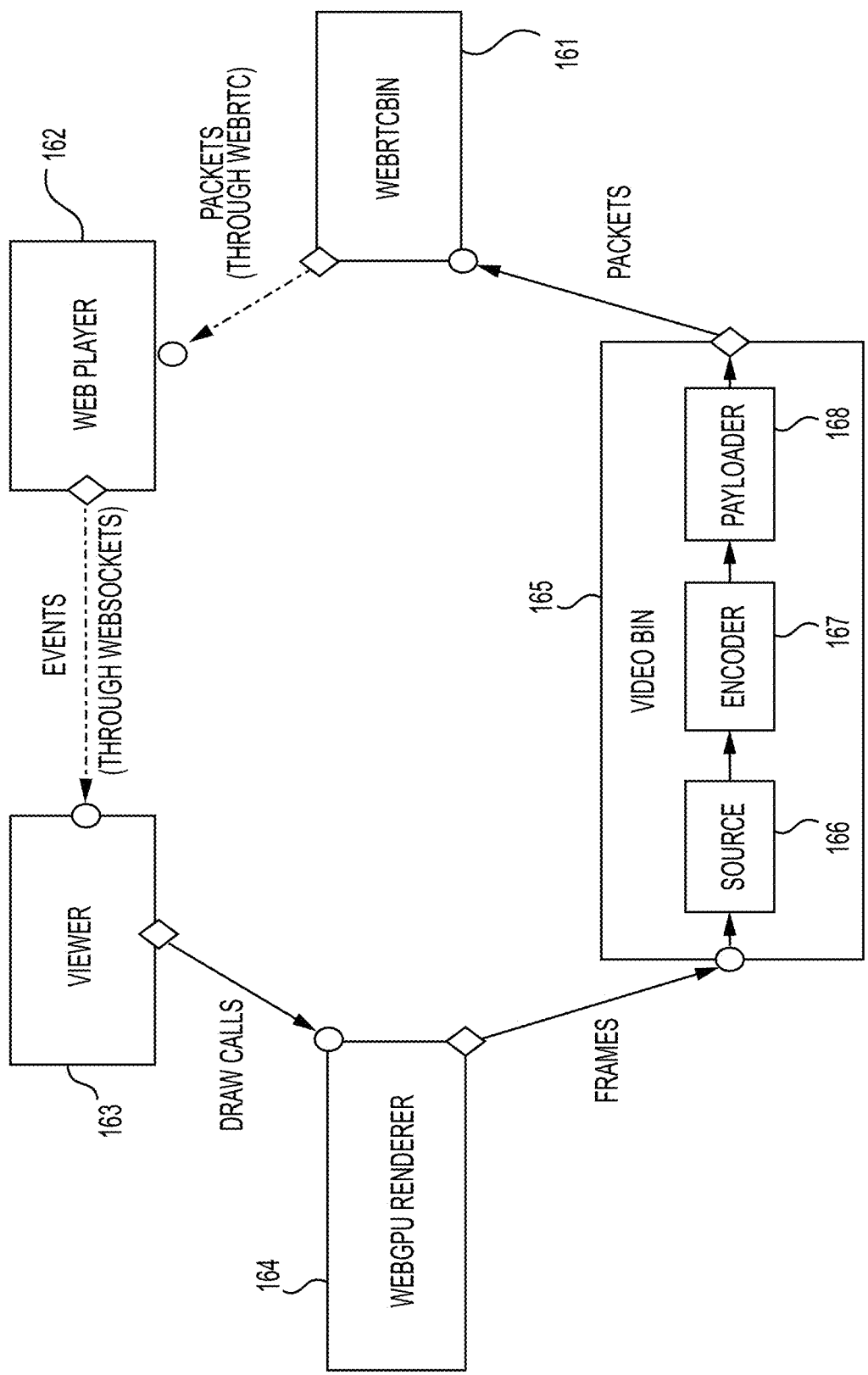
FIG. 16 is an exemplary architecture of a streaming viewer, according to an embodiment of the present disclosure.

The architecture of an exemplary embodiment of a streaming slide viewer is illustrated in FIG. 16. Different pieces, indicated as "bins" refer to streamer library components.

In the exemplary embodiment, the user's browser may receive a video feed through WebRTC, and sends back events corresponding to user interactions with the viewer 163 for the server to update the FOV accordingly.

The WebRTCB in 161 may send packets to a Web Player 162 through WebRTC. The Web Player 162 in turn may send events through WebSockets to the Viewer 163. The Viewer 163 may draw calls from a WebGPU Renderer 164. Frames may be sent from the WebGPU Renderer 164 to a video bin 165, which FFGI may include a source 166, an encoder 167, and a payloader 168.

The exemplary embodiment may be easy to implement, based on the ecosystem of plugins for GStreamer, as well as the quality of integration of GStreamer with Rust. Running the same code natively and in the browser ensures that the behavior of the viewer remains the same between all its rendering backends.

It should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Thus, while certain embodiments have been described, those skilled in the art will recognize that other and further modifications may be made thereto without departing from the spirit of the invention, and it is intended to claim all such changes and modifications as falling within the scope of the invention. For example, functionality may be added or deleted from the block diagrams and operations may be interchanged among functional blocks. Steps may be added or deleted to methods described within the scope of the present invention.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations are possible within the scope of the disclosure. Accordingly, the disclosure is not to be restricted except in light of the attached claims and their equivalents.

What is claimed is:

1. A computer-implemented method for processing an electronic image, the method comprising:
   receiving, by a slide viewer running on a web browser, the electronic image and a FOV (field of view) of the electronic image, wherein the FOV includes at least one coordinate, at least one dimension, and a magnification factor;
   loading, by the slide viewer, a plurality of tiles within the FOV;
   determining, by the slide viewer, a state of loading of the plurality of tiles in a cache from a storage device;
   determining, by the slide viewer, whether the cache has a maximum occupancy;
   in response to determining that the cache has the maximum occupancy, sorting, by the slide viewer, the cache based on the FOV; and
   in response to determining that the state of the plurality of tiles in the cache is a fully loaded state, rendering, by the slide viewer, the plurality of tiles to a display.

2. The computer-implemented method of claim 1, further comprising:
   determining, by the slide viewer, that the state of loading of a tile of the plurality of tiles in the cache is a tile request state;
   in response to the determining, sending, by the slide viewer, the tile request state to a tile server;
   receiving, by the slide viewer, a data transfer from the tile server, the data transfer responsive to the tile server receiving the tile request state, wherein the data transfer includes tile data corresponding to the tile of the plurality of tiles;
   moving, by the slide viewer, the tile of the plurality of tiles to the fully loaded state; and
   rendering, by the slide viewer, the plurality of tiles.

3. The computer-implemented method of claim 1, wherein receiving the electronic image includes loading, by the slide viewer, a set of tiles into the cache at a lower magnification level than a default magnification level for display.

4. The computer-implemented method of claim 1, the loading the plurality of tiles within the FOV of the electronic image further comprising:
   determining, by the slide viewer, whether the cache stores a tile of the plurality of tiles;
   in response to determining that the cache stores the tile, determining, by the slide viewer, whether the tile has a magnification level equal or greater than the magnification factor; and
   in response to determining that the tile does have the magnification level equal or greater than the magnification factor, loading, by the slide viewer, the tile from the cache.

5. The computer-implemented method of claim 4, further comprising:
   in response to determining that the tile does not have the magnification level equal or greater than the magnification factor, retrieving, by the slide viewer, a stored tile corresponding to the tile of the plurality of tiles, where the stored tile has a highest stored magnification level.

6. The computer-implemented method of claim 1, wherein the electronic image is a WSI (whole slide image).

7. The computer-implemented method of claim 6, wherein the WSI includes a pyramidal structure of a plurality of images, the pyramidal structure of the plurality of images including at least one WSI magnification level, wherein the at least one WSI magnification level includes a set of tiles corresponding to the magnification factor.

8. The computer-implemented method of claim 1, the sorting the cache based on the FOV of the electronic image further comprising:
   leaving, by the slide viewer, at least one tile of the plurality of tiles stored in the cache, the leaving according to an order of priority, wherein the leaving continues until the cache is at or below the maximum occupancy; and
   in response to determining that the cache is at or below the maximum occupancy, removing, by the slide viewer, any remaining tiles of the plurality of tiles from the cache.

9. The computer-implemented method of claim 8, wherein the order of priority includes a FOV tile with a magnification level equal or greater than the magnification factor, a FOV bordering tile with the magnification level equal or greater than the magnification factor, a plurality of FOV tiles with the magnification level less than the magnification factor in a descending magnification level order, and at least one other tile.

10. A computer system for processing an electronic image, the computer system comprising:
    at least one memory storing instructions; and
    at least one processor configured to execute the instructions to perform operations comprising:
      receiving, by a slide viewer running on a web browser, the electronic image and a FOV (field of view) of the electronic image, wherein the FOV includes at least one coordinate, at least one dimension, and a magnification factor;
      loading, by the slide viewer, a plurality of tiles within the FOV of the electronic image, the loading further comprising:
        determining, by the slide viewer, whether a cache stores a tile of the plurality of tiles;
        in response to determining that the cache stores the tile, determining, by the slide viewer, whether the tile has a magnification level equal or greater than the magnification factor; and
        in response to determining that the tile does have the magnification level equal or greater than the magnification factor, loading, by the slide viewer, the tile from the cache and in response to determining that the tile does not have the magnification level equal or greater than the magnification factor, retrieving, by the slide viewer, a stored tile corresponding to the tile of the plurality of tiles, where the stored tile has a highest stored magnification level;
      determining, by the slide viewer, a state of loading of the plurality of tiles in a cache from a storage device; and
      in response to determining that the state of the plurality of tiles in the cache is a fully loaded state, rendering, by the slide viewer, the plurality of tiles to a display.

11. The computer system of claim 10, further comprising:
    determining, by the slide viewer, that the state of loading of a tile of the plurality of tiles in the cache is a tile request state;
    in response to the determining, sending, by the slide viewer, the tile request state to a tile server;
    receiving, by the slide viewer, a data transfer from the tile server, the data transfer responsive to the tile server receiving the tile request state, wherein the data transfer includes tile data corresponding to the tile of the plurality of tiles;

moving, by the slide viewer, the tile of the plurality of tiles to the fully loaded state; and rendering, by the slide viewer, the plurality of tiles.

12. The computer system of claim 10, wherein receiving the electronic image includes loading, by the slide viewer, a set of tiles into the cache at a lower magnification level than a default magnification level for display.

13. The computer system of claim 10, wherein the electronic image is a WSI (whole slide image).

14. A non-transitory computer-readable medium storing instructions that, when executed by a processor, cause the processor to perform operations for processing an electronic image, the operations comprising:

receiving, by a slide viewer running on a web browser, the electronic image and a FOV (field of view) of the electronic image, wherein the FOV includes at least one coordinate, at least one dimension, and a magnification factor;

loading, by the slide viewer, a plurality of tiles within the FOV;

determining, by the slide viewer, a state of loading of the plurality of tiles in a cache from a storage device;

determining, by the slide viewer, whether the cache has a maximum occupancy; and in response to determining that the cache has the maximum occupancy, sorting, by the slide viewer, the cache based on the FOV; and in response to determining that the state of the plurality of tiles in the cache is a fully loaded state, rendering, by the slide viewer, the plurality of tiles to a display.

15. The non-transitory computer-readable medium of claim 14, the sorting the cache based on the FOV of the electronic image further comprising:

leaving, by the slide viewer, at least one tile of the plurality of tiles stored in the cache, the leaving according to an order of priority, wherein the leaving continues until the cache is at or below the maximum occupancy; and in response to determining that the cache is at or below the maximum occupancy, removing, by the slide viewer, any remaining tiles of the plurality of tiles from the cache.

16. The non-transitory computer-readable medium of claim 15, wherein the order of priority includes a FOV tile with a magnification level equal or greater than the magnification factor, a FOV bordering tile with the magnification level equal or greater than the magnification factor, a plurality of FOV tiles with the magnification level less than the magnification factor in a descending magnification level order, and at least one other tile.

17. A computer-implemented method for processing an electronic image, the method comprising:

receiving, by a slide viewer running on a web browser, the electronic image and a FOV (field of view) of the electronic image, wherein the FOV includes at least one coordinate, at least one dimension, and a magnification factor;

loading, by the slide viewer, a plurality of tiles within the FOV, the loading further comprising:

determining, by the slide viewer, whether a cache stores a tile of the plurality of tiles;

in response to determining that the cache stores the tile, determining, by the slide viewer, whether the tile has a magnification level equal or greater than the magnification factor; and in response to determining that the tile does have the magnification level equal or greater than the magnification factor, loading, by the slide viewer, the tile from the cache and in response to determining that the tile does not have the magnification level equal or greater than the magnification factor, retrieving, by the slide viewer, a stored tile corresponding to the tile of the plurality of tiles, where the stored tile has a highest stored magnification level;

determining, by the slide viewer, a state of loading of the plurality of tiles in a cache from a storage device; and in response to determining that the state of the plurality of tiles in the cache is a fully loaded state, rendering, by the slide viewer, the plurality of tiles to a display.

18. A computer-implemented method for processing an electronic image, the method comprising:

receiving, by a slide viewer running on a web browser, the electronic image and a FOV (field of view) of the electronic image, wherein the FOV includes at least one coordinate, at least one dimension, and a magnification factor, wherein the electronic image is a WSI (whole slide image), wherein the WSI includes a pyramidal structure of a plurality of images, the pyramidal structure of the plurality of images including at least one WSI magnification level, wherein the at least one WSI magnification level includes a set of tiles corresponding to the magnification factor;

loading, by the slide viewer, a plurality of tiles within the FOV;

determining, by the slide viewer, a state of loading of the plurality of tiles in a cache from a storage device; and in response to determining that the state of the plurality of tiles in the cache is a fully loaded state, rendering, by the slide viewer, the plurality of tiles to a display.

* * * * *